(12) United States Patent
Nugent et al.

(10) Patent No.: US 9,023,377 B2
(45) Date of Patent: May 5, 2015

(54) METHODS AND COMPOSITIONS FOR ENHANCING VASCULAR ACCESS

(71) Applicants: Helen Marie Nugent, Needham, MA (US); Elazer Edelman, Brookline, MA (US)

(72) Inventors: Helen Marie Nugent, Needham, MA (US); Elazer Edelman, Brookline, MA (US)

(73) Assignee: Shire Regenerative Medicine, Inc.

( * ) Notice: Subject to any disclaimer, the term of this patent is extended or adjusted under 35 U.S.C. 154(b) by 0 days.

(21) Appl. No.: 13/667,227

(22) Filed: Nov. 2, 2012

(65) Prior Publication Data
US 2013/0210142 A1  Aug. 15, 2013

Related U.S. Application Data

(63) Continuation of application No. 11/922,729, filed as application No. PCT/US2006/021755 on Jun. 5, 2006, now abandoned, which is a continuation of application No. PCT/US2005/043967, filed on Dec. 5, 2005.

(60) Provisional application No. 60/682,708, filed on May 20, 2005.

(51) Int. Cl.
*A61F 2/02* (2006.01)
*C12N 5/071* (2010.01)
*A61L 27/38* (2006.01)

(52) U.S. Cl.
CPC ............ *C12N 5/069* (2013.01); *A61L 27/3808* (2013.01)

(58) Field of Classification Search
None
See application file for complete search history.

(56) References Cited

U.S. PATENT DOCUMENTS

| | | | |
|---|---|---|---|
| 4,418,691 A | 12/1983 | Yannas et al. | |
| 4,732,155 A | 3/1988 | Zetter et al. | |
| 4,787,900 A | 11/1988 | Yannas | |
| 4,820,626 A | 4/1989 | Williams et al. | |
| 5,037,378 A | 8/1991 | Muller et al. | |
| 5,073,492 A * | 12/1991 | Chen et al. | 435/384 |
| 5,122,110 A * | 6/1992 | McNally et al. | 600/36 |
| 5,202,120 A | 4/1993 | Silver et al. | |
| 5,399,665 A | 3/1995 | Barrera et al. | |
| 5,455,039 A | 10/1995 | Edelman et al. | |
| 5,527,532 A | 6/1996 | Edelman et al. | |
| 5,540,928 A | 7/1996 | Edelman et al. | |
| 5,567,612 A | 10/1996 | Vacanti et al. | |
| 5,575,815 A | 11/1996 | Slepian et al. | |
| 5,716,404 A | 2/1998 | Vacanti et al. | |
| 5,736,372 A | 4/1998 | Vacanti et al. | |
| 5,739,113 A | 4/1998 | Lee | |
| 5,759,830 A | 6/1998 | Vacanti et al. | |
| 5,766,584 A | 6/1998 | Edelman et al. | |
| 5,770,193 A | 6/1998 | Vacanti et al. | |
| 5,770,417 A | 6/1998 | Vacanti et al. | |
| 5,804,178 A | 9/1998 | Vacanti et al. | |
| 5,843,156 A | 12/1998 | Slepian et al. | |
| 5,855,610 A | 1/1999 | Vacanti et al. | |
| 5,879,713 A | 3/1999 | Roth et al. | |
| 5,914,268 A | 6/1999 | Keller et al. | |
| 6,068,837 A | 5/2000 | Shockley et al. | |
| 6,139,574 A | 10/2000 | Vacanti et al. | |
| 6,140,039 A | 10/2000 | Naughton et al. | |
| 6,156,572 A | 12/2000 | Bellamkonda et al. | |
| 6,281,015 B1 | 8/2001 | Mooney et al. | |
| 6,290,729 B1 | 9/2001 | Slepian et al. | |
| 6,309,635 B1 | 10/2001 | Ingber et al. | |
| 6,328,762 B1 | 12/2001 | Anderson et al. | |
| 6,348,069 B1 | 2/2002 | Vacanti et al. | |
| 6,358,989 B1 | 3/2002 | Kunz et al. | |
| 6,506,398 B1 | 1/2003 | Tu et al. | |
| 6,528,080 B2 | 3/2003 | Dunn et al. | |
| 6,569,441 B2 | 5/2003 | Kunz et al. | |
| 6,615,071 B1 | 9/2003 | Casscells, III et al. | |
| 6,676,971 B2 | 1/2004 | Goupil et al. | |

(Continued)

FOREIGN PATENT DOCUMENTS

| | | |
|---|---|---|
| AU | 2005/314263 | 6/2006 |
| AU | 2005/314312 | 6/2006 |

(Continued)

OTHER PUBLICATIONS

Baust et al., "Cell Viability Improves Following Inhibition of Cryopreservation-Induced Apoptosis", In Vitro Cellular & Developmental Biology—Animal, 36(4):262-270, (2000).
Babaei, et al., "Role of Nitric Oxide in the Angiogenic Response in Vitro to Basic Fibroblast Growth Factor," Circ. Res., 82:1007-1015 (1998).

(Continued)

*Primary Examiner* — Allison Fox
*Assistant Examiner* — Yvonne Pyla
(74) *Attorney, Agent, or Firm* — K&L Gates LLP

(57) ABSTRACT

Disclosed is an implantable material comprising a biocompatible matrix and cells which, when provided to a vascular access structure, can promote functionality generally. For example, implantable material of the present invention can enhance maturation of an arteriovenous native fistula as well as prolong the fistula in a mature, functional state suitable for dialysis. Additionally, the present invention can promote formation of a functional arteriovenous graft suitable for dialysis as well as promote formation of a functional peripheral bypass graft. Implantable material can be configured as a flexible planar form or a flowable composition with shape-retaining properties suitable for implantation at, adjacent or in the vicinity of an anastomoses or arteriovenous graft. According to the methods disclosed herein, the implantable material is provided to an exterior surface of a blood vessel. Certain embodiments of the flexible planar form define a slot. The materials and methods of the present invention comprise cells, preferably endothelial cells or cells having an endothelial-like phenotype.

17 Claims, 6 Drawing Sheets

(56) References Cited

U.S. PATENT DOCUMENTS

| | | | |
|---|---|---|---|
| 6,723,131 | B2 | 4/2004 | Muschler |
| 6,726,923 | B2 | 4/2004 | Iyer et al. |
| 6,730,298 | B2 | 5/2004 | Griffith-Cima et al. |
| 6,755,853 | B2 | 6/2004 | McKenzie et al. |
| 6,852,537 | B2 * | 2/2005 | Hebbel et al. ............... 435/402 |
| 6,886,568 | B2 | 5/2005 | Frondoza et al. |
| 6,911,216 | B1 | 6/2005 | Roth et al. |
| 7,011,677 | B2 | 3/2006 | Wallace et al. |
| 7,037,332 | B2 | 5/2006 | Kutryk |
| 2001/0036451 | A1 | 11/2001 | Goupil et al. |
| 2002/0042130 | A1 | 4/2002 | Hebbel et al. |
| 2002/0049495 | A1 | 4/2002 | Kutryk et al. |
| 2002/0061303 | A1 | 5/2002 | Singh |
| 2002/0077694 | A1 | 6/2002 | McKenzie et al. |
| 2002/0090398 | A1 | 7/2002 | Dunn et al. |
| 2002/0120123 | A1 * | 8/2002 | Rosen et al. ............... 536/23.5 |
| 2002/0123809 | A1 | 9/2002 | Tai et al. |
| 2003/0163192 | A1 | 8/2003 | Wallace et al. |
| 2004/0047843 | A1 | 3/2004 | Meythaler et al. |
| 2004/0156878 | A1 | 8/2004 | Rezania et al. |
| 2005/0008629 | A1 | 1/2005 | Arm |
| 2005/0106554 | A1 | 5/2005 | Palecek et al. |
| 2007/0088252 | A1 | 4/2007 | Pestotnik et al. |
| 2007/0106244 | A1 | 5/2007 | Mosler et al. |
| 2008/0119946 | A1 | 5/2008 | Nugent et al. |

FOREIGN PATENT DOCUMENTS

| | | |
|---|---|---|
| CA | 2589588 | 6/2006 |
| CA | 2589597 | 6/2006 |
| CA | 2589871 | 6/2006 |
| EP | 0 341 006 | 11/1989 |
| EP | 0 518 389 | 12/1992 |
| EP | 1269840 | 1/2003 |
| EP | 1824526 | 8/2007 |
| EP | 1824529 | 8/2007 |
| WO | 93/02188 | 2/1993 |
| WO | 93/14193 | 7/1993 |
| WO | 94/22505 | 10/1994 |
| WO | 95/29713 | 11/1995 |
| WO | 01/62241 | 8/2001 |
| WO | 0170021 | 9/2001 |
| WO | 02/07749 | 1/2002 |
| WO | 02/058588 | 8/2002 |
| WO | 02/062335 | 8/2002 |
| WO | 02/068010 | 9/2002 |
| WO | 03/026489 | 4/2003 |
| WO | 03/060062 | 6/2003 |
| WO | 03/083044 | 10/2003 |
| WO | 2004/002549 | 1/2004 |
| WO | 2004/033674 | 4/2004 |
| WO | 2005/003317 | 1/2005 |
| WO | 2005/032618 | 4/2005 |
| WO | 2005/072417 | 8/2005 |
| WO | 2005/108559 | 11/2005 |
| WO | 2005/120431 | 12/2005 |
| WO | 2006/050063 | 5/2006 |
| WO | 2006/062871 | 6/2006 |
| WO | 2006/062909 | 6/2006 |
| WO | 2006/062962 | 6/2006 |
| WO | 2006/116357 | 11/2006 |
| WO | 2006/120461 | 11/2006 |
| WO | 2007/001744 | 1/2007 |
| WO | 2007/047425 | 4/2007 |

OTHER PUBLICATIONS

Bernemann, et al., "Improvement of the cryopreservation of 293T-cell seeded 3D collagen scaffolds," Journal of Biomechanics, 39:S383 (2006).
Bjornsson, et al., "Acidic Fibroblast Growth Factor Promotes Vascular Repair," Proc. Natl. Acad. Sci. USA, 88:8651-8655 (1991).
Burdick et al., "Photoencapsulation of Osteoblasts in Injectable RGD-modified PEG Hydrogels for Bone Tissue Engineering," Biomaterials, 23: 4315-23 (2002).
Castellot, et al., "Cultured Endothelial Cells Produce a Heparinlike Inhibitor of Smooth Muscle Cell Growth," J. of Cell Biology, 90:372-379 (1981).
Centra, et al., "Culture of Bovine pulmonary artery endothelial cells on gelfoam blocks," Faseb J., 6(12):3117-3121, (1992).
Clowes, et al., "Kinetics of Cellular Proliferation After Arterial Injury I: Smooth Muscle Growth in the Absence of Endothelium," Lab Invest., 49:327-333 (1983).
Cochlovius, et al., "Therapeutic Antibodies," Modern Drug Discovery, 33-38 (2003).
Conte, et al., "Efficient Repopulation of Denuded Rabbit Arteries With Autologous Genetically Modified Endothelial Cells," Circ., 89:2161-69 (1994).
Conte, et al., "Endothelial Cell Seeding Fails to Attenuate Intimal Thickening in Balloon Injured Rabbit Arteries," J. Vasc. Surg., 21(3):413-421 (Mar. 1995).
Cooke, et al., "Cellular Mechanisms of Atherogenesis and the effects of Nitric Oxide," Curr. Opin. Cardiol., 7:799-804 (1992).
Dodge, et al., "Density-Dependent Endothelial Cell Production of an Inhibitor of Smooth Muscle Cell Growth," J. Cell. Biochem., 53:21-31 (1993).
Edelman, et al., "Effect of Controlled Adventitial Heparin Delivery on Smooth Muscle Cell Proliferation Following Endothelial injury," Proc. Natl. Acad. Sci (USA), 87:3773-3777 (1990).
Edelman, et al., "Basic Fibroblast Growth Factor Enhances the Coupling of Intimal Hyperplasia and Proliferation of Vasa Vasorum in Injured Rat Arteries," J. Clin. Invest., 89:465-473 (1992).
Edelman, et al., "Contrasting Effects of the Intermittent and Continuous Administration of Heparin in Experimental Restenosis," Circ., 89(2):770-776 (1992).
Edelman, et al., "Perivascular and Intravenous Administration of Basic Fibroblast Growth Factor: Vascular and Solid Organ Deposition," Proc. Natl. Acad. Sci. (USA), 90:1513-1517 (1993).
Edelman, et al., "Protamine and Protamine-Insulins Exacerbate the Vascular Response to Injury," J. Clin. Invest., 91:2308-2313 (1993).
Edelman, et al., "Tissue Engineered Endothelial Cell Implants and Proliferative Vascular Disease," Circ., 92 (8):I-748 (1995).
Ellis, et al., "Effect of 18- to 24-hour Heparin Administration for Prevention of Restenosis After Uncomplicated Coronary Angioplasty," Am. Heart. J., 117(4):777-782 (1989).
Esko, "Animal Cell Mutants Defective in Heparan Sulfate Polymerization," Heparin and Related Polysaccharides, (Lane, Bjork & Lindahl, Eds.), Plenum Press, pp. 97-106 (1992).
Farndale, et al., "Improved Quantitation and Discrimination of Sulphated Glycosaminoglycans by Use of Dimethylmethylene Blue," Biochem. et Biophys. Acta, 883:173-177 (1986).
Fishman, et al., "Endothelial Regeneration in the Rat Carotid Artery and the Significance of Endothelial Denudation in the Pathogenesis of Myointimal Thickening," Lab. Invest, 32(3):339-351 (1975).
Gimbrone, "Culture of Vascular Endothelium," Prog. Hemo. and Thromb., 3:1-28 (1976).
Han, et al, "Heparin/heparin sulfate chelation inhibits control of vascular repair by tissue-engineered endothelial cells," Am. J. Physiology, 273(6):H2586-95 (1997).
Hazinedaroglu et al., "Immediate postimplant hemodialysis through a new 'self-sealing' herparin-bonded polycarbonate/urethane graft," Transplantation Proceedings, 36(9):2599-2602 (2004).
Hirigoyen et al., "Periadventitial delivery of heparin in the prevention of micovenous thrombosis," J. Oral and Maxillofacial Surg., 54(9):1097-1102, (1996).
Jarrell et al., "Use of endothelial monolayer on a vascular graft prior to implantation. Temporal dynamics and compatibility with the operating room." Annals of Surg., 203(6):671-678, (1986).
Lee, et al., "Endothelial Cell Seeding Onto the Extracellular Matrix of Fibroblasts for the Development of a Small Diameter Polyurethane Vessel," ASAIO J., 39(3):M740-M745, 1993.
Lehmann, et al., "Paradoxical Increase in Restenosis Rate With Chronic Heparin Use: Final Results of a Randomized Trial," J. Am. Coll. Cardiol., 17(7):181A (Abstract) (1991).
Lidington, et al., "A comparison of primary endothelial cell lines for studies of immune interactions," Transplant Immunol, 7(4):239-246, (1999).

(56) References Cited

OTHER PUBLICATIONS

Martin et al. "The role of bioreactors in tissue engineering," Trends in Biochemistry, 22(2):80-86 (2004).
McNamara, et al., "L-Arginine Inhibits Balloon Catheter-Induced Intimal Hyperplasia," Biochem. Biophys. Res. Comm., 193 (1):291-296 (1993).
Mestas, et al., "Of Mice and Not Men: Differences Between Mouse and Human Immunology," 172:2731-2738 (2004).
Methe, et al., "Matrix embedding alters the immune response against endothelial cells in vitro and in vivo," Circ., 112(9 Supp.):I89-I95, (2005).
Methe, et al., "Cell-matrix contact prevents recognition and damage of endothelial cells in states of heightened immunity," Circ., 114(1 Supp.):I233-I238, (2006).
Moncada, et al., "The L-Arginine-Nitric Oxide Pathway," N. Engl. J. Med., 329(27):2002-2012 (1993).
Montañez, et al., "Comparative Study of Tube Assembly in Three-Dimensional Collagen Matrix and on Matrigel Coats," Angiogenesis, 5:167-172 (2002).
Montesano, et al., "Basic Fibroblast Growth Factor Induces Angiogenesis in Vitro," Proc. Natl. Acad. Sci. USA, 83:7297-7301 (1986).
Nathan, et al., "Perivascular Heparin Delivery Using Biodegradable Polymers," Polymeric Materials Science and Engineering, 70:320-321 (Proceedings of the American Chemical Society, Spring Meeting 1994).
Nathan, et al., "Tissue Engineered Perivascular Endothelial Cell Implants Regulate Vascular Injury," Proc. Natl. Acad. Sci. (USA), 92:8130-8134 (1995).
Nissen SE. "Pathobiology, Not Angiography, Should Guide Management in Acute Coronary Syndrome/Non-ST-Segment Elevation Myocardial Infarction," J. Am. College of Cardio, 41(5):103S-112S (2003).
Nugent, et al., "Vascular Cell-Derived Heparan Sulfate Shows Coupled Inhibition of Basic Fibroblast Growth Factor Binding and Mitogenesis in Vascular Smooth Muscle Cells," Circ. Res., 73(6):1051-1060 (1993).
Nugent, et al., "Local Drug Delivery and Tissue Engineering Regulate Vascular Injury," Cur. Pharm. Des. 3(6):529-544 (1997).
Nugent, et al., "Endothelial implants inhibit intimal hyperplasia after porcine angioplasty," Circ. Res., 84(4):384-391, (1999).
Nugent, et al., "Perlecan is required to inhibit thrombosis after deep vascular injury and contributes to endothelial cell-mediated inhibition of intimal hyperplasia," PNAS, 97(12):6722-6727 (2000).
Nugent, et al., "Endothelial Implants Provide Long-Term Control of Vascular Repair in a Porcine Model of Arterial Injury," J. Surg. Res., 99:228-234 (2001).
Nugent, et al., "Transplanted Endothelial Cells Control Repair in Complex Models of Vascular Injury," Circ., 104(17):II-16-17 (2001).
Nugent, et al.,"Practices and Considerations in the Development of an Allogeneic Cellular Transplant," BioPharm, 14(1):1-5 (2001).
Nugent, et al., "Perivascular endothelial implants inhibit intimal hyperplasia in a model of arteriovenous fistulae: A safety and efficacy study in the pig," J. Vasc. Res., 39(6):524-533, (2002).
Parikh, et al., "Endothelial cell delivery for cardiovascular therapy," ADV. Drug Delivery Rev., 42:139-161 (2000).
Pascual, et al., "Restoring the endothelium of cryopreserved arterial grafts: co-culture of venous and arterial endothelial cells," Cryobiology, 49(3):272-285 (2004).
Rahmanian, et al., "Testicular Hyaluronidase Induces Tubular Structures of Endothelial Cells Grown in Three-Dimensional Collagen Gel through a CD44-Mediated mechanism," Int. J. Cancer, 97:601-607 (2002).
Rapraeger, et al., "A Quantative Solid-Phase Assay for Identifying Radiolabeled Glycosaminoglycans in Crude Cell Extracts," Analytical Biochem., 179(2):361-365 (1989).
Reidy, et al., "Factors Controlling Smooth-Muscle Cell Proliferation," Arch. Pathol. Lab. Med., 116:1276-80 (1992).
Reidy, et al., "Neointimal Proliferation: the Role of Basic FGF on Vascular Smooth Muscle Cell Proliferation," Thromb. Haemost., 70(1):172-176 (1993).
Satake, et al., "Angiogenic Stimuli Are Essential for Survival of Vascular Endothelial Cells in Three-Dimensional Collagen Lattice," Biochem. Biopys. Res. Comm., 244:642-646 (1998).
Schwartz, et al., "The Aortic Intima; II. Repair of the Aortic Lining after Mechanical Denudation," Am. J. Pathol., 81:15-42 (1975).
Stone, et al., "Effect of endothelial shear stress on the profession of coronary artery disease, vascular remodeling, and in-stent restenosis in humans: in-vivo 6-month follow-up study," Circ., 108(4):438-444, (2003).
Tufveson, et al., "New Immunosuppressants: Testing and Development in Animal Models and the Clinic: with Special Reference to DSG," Immun. Review, 136: 101-107 (1993).
Westerband, et al., "Immunocytochemical Determination of Cell Type and Proliferation Rate in Human Vein Graft Stenoses," J. Vasc. Surg., 25: 64-73 (1997).
Zarge, et al., "Fibrin glue containing fibroblast growth factor type 1 and heparin with autologous endothelial cells reduces intimal hyperplasia in a canine carotid artery balloon injury model," J. Vasc. Surg., 25:840-849 (1997).
Sekiguchi, et al. "Neural stem cells contribute to peripheral nerve repair by coordinated angiogenesis and neurogenesis," Circulation. 116:II_79 (2007).
Zavan, et al. "New 3D hyaluronan-based scaffold for in vitro reconstruction of the rat sciatic nerve," Neurological Research-Neuromyology, 30(2):190-6 (2008).
Galis et al., "Matrix Metalloproteinases in Vascular Remodeling and Atherogenesis: The Good, the Bad and the Ugly," Circ. Res. 90:251-262 (2002).
Huynh et al., "Remodeling of an Acellular Collagen Graft Into a Physiologically Responsive Neovessel," Nature Biotechnology, 17: 1083-1086 (1999).
McGrath et al., "New aspects of vascular remodeling: the involvement of all vascular cell types," Exp. Physiol. 90(4): 469-475 (2005).
Misra et al., "Adventitual remodeling with increased matrix metalloproteinase-2 activity in a porcine arteriovenous polytetrafluoroethylene grafts," Kidney Int., 68(6): 2890-2900 (2005).
Nagase et al., "Matrix Metalloproteinases," J. Biol. Chem., 274(31): 21491-21494 (1999).
Whatling et al., "Matrix Management: Assignment Different Roles for MMP-2 and MMP-9 in Vascular Remodeling," Arterioscler. Thromb. Vasc. Biol., 24:10-11 (2004).
ATCC Primary Cell Solutions Media, Supplements and Reagents Endothelial Cell Growth Kit-VEGF, Retrieved from the Internet: URL:http://www.lgcstandards-atcc.org/SGCAdvancedCatalogue Search/ProductDescription/tabid/1068/Default.
aspx?ATCCNum=PCS-100-041
&Template=primaryCellMediaReagents [retrieved on May 25, 2011].
Cucina, "Vascular endothelial growth factor increases the migration and proliferation of smooth muscle cells through the mediation of growth factors released by endothelial cells," Journal of Surgical Research, 109(1): 16-23 (2003).
Dorafshar, "Vascular endothelial growth factor inhibits mitogen-induced vascular smooth muscle cell proliferation," Journal of Surgical Research, 114(2): 179-186 (2003).
Kraling, et al., "A simplified method for growth of human microvascular endothelial cells results in decreased senescence and continued responsiveness to cytokines and growth factors," In Vitro Cellular & Developmental Biology—Animal, 34(4): 308-315 (1998).
Luo, et al., "Reduction of vein graft intimal hyperplasia and preservation of endothelium-dependent relaxation by topical vascular endothelial growth factor," Journal of Vascular Surgery, C.V. Mosby Co., St. Louis, MO, US, 27(1): 167-173 (1998).
Simper, et al., "Smooth muscle progenitor cells in human blood," Circulation, Lippincot Williams and Wilkins, Baltimore, US, 106(10): 1199-1204 (2002).

* cited by examiner

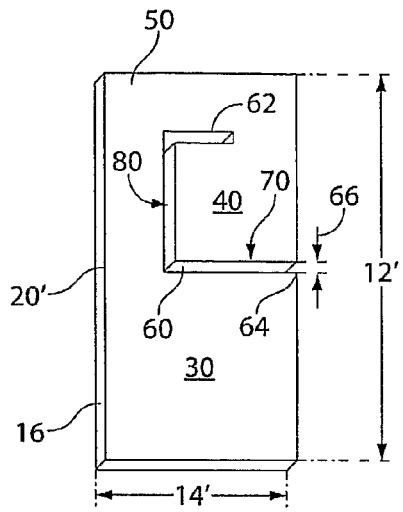
Fig. 2A
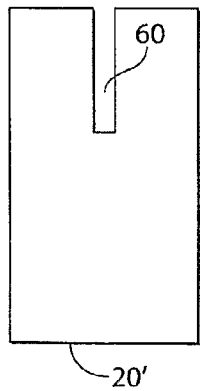 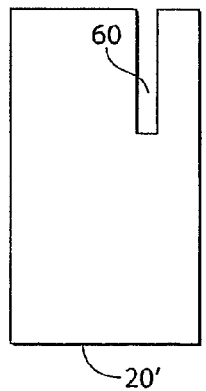 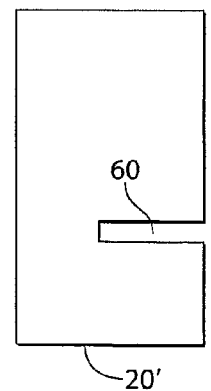 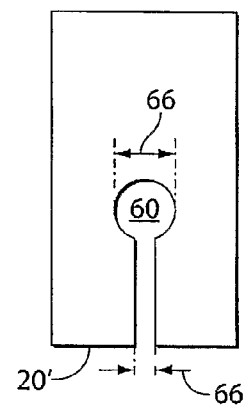
Fig. 2B　　Fig. 2C　　Fig. 2D　　Fig. 2E
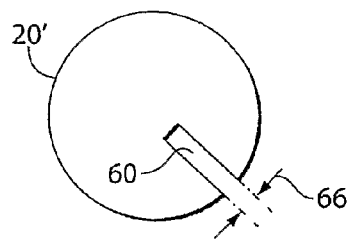 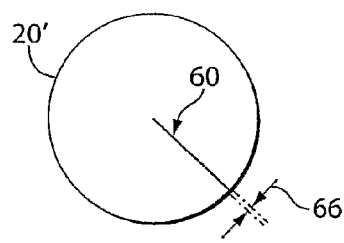
Fig. 2F　　　　Fig. 2G

METHODS AND COMPOSITIONS FOR ENHANCING VASCULAR ACCESS

RELATED APPLICATIONS

This application is a continuation of the U.S. patent application Ser. No. 11/922,729, filed Aug. 13, 2008, which is the national phase of International (PCT) Patent Application Serial No. PCT/US2006/021755, filed Jun. 5, 2006, published under PCT Article 21(2) in English, which claims priority to and the benefit under 35 U.S.C. Section 119(e) of U.S. Provisional Patent Application No. 60/692,708, filed Jun. 21, 2005 and PCT International Patent Application No. PCT/US2005/043967, filed Dec. 6, 2005, the disclosures of each of which are incorporated herein by reference.

BACKGROUND OF THE INVENTION

Vascular access failure is the major complication in providing care to patients on hemodialysis to treat end stage renal disease (ESRD). The rate of existing ESRD cases in the United Sates has increased each year since 1980. In 2001 the prevalent rate reached almost 1,400 patients per million population, a 2.4 percent increase from the previous year. Based on demographic changes in age, race, ethnicity and diabetic status, the prevalent ESRD population in the US is expected to grow to 1.3 million by 2030. Currently, approximately 65% of the prevalent ESRD population are treated with hemodialysis (approximately 264,710 patients). Between 1997 and 2001, the prevalent hemodialysis population grew 4.5% per year. Using Medicare data, it has been determined that by 2001 the total ESRD costs reached $15.5 billion, 6.4% of the entire Medicare budget of $242 billion (total costs reached $22.8 billion from all sources). Indeed, the annual cost of vascular access related morbidity in the US currently exceeds 1 billion dollars per year.

Vascular access failure is the single most important cause of morbidity in the hemodialysis population. A recent report analyzing US Renal Data System (USRDS) data found an overall primary unassisted access patency rate of only 53% at 1 year. The 1-year primary unassisted access patency rates were 49% for vascular access structures such as arteriovenous grafts involving ePTFE® prosthetic bridges and 62% for arteriovenous (AV) fistulae. Cumulative patency rates for first time accesses at 1, 3 and 5 years were 54%, 46% and 36% for lower-arm fistulae and 54%, 28% and 0% for AV grafts, respectively. Currently, the use of grafts involving ePTFE prosthetic bridges accounts for 70% of all hemodialysis access procedures in the United States, the National Kidney Foundation currently recommends that AV fistula be the preferred method of vascular access. It is expected that there will be an increase in the proportion of new AV fistulae in the US in the future.

Autogenous arteriovenous fistulae have historically been regarded as the best choice for vascular access in hemodialysis patients. When an AV fistula successfully matures after surgical creation, it may function for years with a low risk of complications and a low incidence of revisions. However, the reported rates of AV fistula non-maturation vary widely, but remain about 20-50%. Non-maturation is generally defined as the inability to permit repetitive cannulation of the fistula for dialysis or to obtain sufficient dialysis blood flow within 12 weeks after surgical creation. The occurrence of AV fistula non-maturation can depend, in part, on the quality and size of the vessels used to form the AV fistula. Preoperative assessment of vessel characteristics has been shown to have beneficial effects in identifying suitable vessels for AV fistula creation.

Failure of vascular access structures is attributable to the cumulative effect of a variety of distinct acute and chronic phenomena, especially at the so-called "toe" of the anastomosis and its downstream surrounds. For example, AV grafts may develop graft-associated stenoses and graft-associated occlusions at the anastomoses on the venous anastomotic side. In one published report, histological examination of segments removed from patients with graft-associated, anastomotic stenosis revealed intimal hyperplasia consisting of smooth muscle cells and extracellular matrix. Graft thrombosis may also contribute to vascular access dysfunction in ePTFE dialysis grafts. Moreover, generally isolation of veins and arteries followed by exposure of the vein segment to arterial blood flow and pressure can cause unavoidable ischemia and reperfusion injury. Surgical manipulation such as suturing can also result in direct trauma to the endothelium and smooth muscle cells of the media in both veins and arteries. Injury to the artery and vein endothelium during the creation of a native or graft anastomoses can influence patency and occlusion rates. In addition to the physical trauma associated with cutting and suturing veins and arteries during formation of a vascular access structure, increased wall stress and shear force can also cause physical and/or biochemical injury to the endothelium. It has been suggested that arterial pressure may alter the normal production of endothelial growth regulatory compounds as well as produce morphological and biochemical changes in the media of the vein.

The current therapy for vascular access failure is either surgical revision or angioplasty with or without stenting. Surgical treatment can be risky in these typically multimorbid patients and the long-term results of angioplasty and stenting are generally disappointing due to failure rates of their own. The goal of improved vascular access for hemodialysis purposes as well as for peripheral circulation therefore is to maintain the anatomical integrity of the original graft site to allow for blood flow rates to support dialysis treatment or sufficient blood flow at peripheral bypass sites.

Other factors contributing to successful maturation of a newly created vascular access structure or prolonged maturation of an already-existing vascular access structure remain elusive. Moreover, relatively few randomized clinical trials have been conducted in the field of vascular access failure prevention. Studies that have evaluated the causes of vascular access failure have reached inconsistent conclusions. In fact, at the present time, despite the enormity of this problem, no effective surgical, therapeutic or pharmacologic measures for the prolonged survival of functioning dialysis access fistula are available to clinicians. Clearly a need exists to move ahead in this vital area of patient care.

SUMMARY OF THE INVENTION

The present invention exploits the discovery that an implantable material comprising cells and a biocompatible matrix, when provided locally to a vascular access structure, can promote formation and/or enhance maturation of the structure as well as prolong the structure in a mature, functional state. In accordance with the present invention, the implantable material is located on an exterior surface of a blood vessel at or adjacent or in the vicinity of the vascular access structure. The present invention can effectively promote integration and/or enhance maturation of a newly created vascular access structure; promote and sustain the functional lifetime of an existing, functioning structure; and, can aid in the salvage of a failed or failing structure.

In one aspect, the invention is a method for treating a vascular access structure in a patient comprising the step of locating at, adjacent or in the vicinity of the vascular access structure an implantable material comprising cells and a biocompatible matrix, wherein the implantable material is effective to promote functionality of said structure. According to certain embodiments described below, the vascular access structure is for dialysis.

According to various embodiments, the vascular access structure is an arteriovenous native fistula, an arteriovenous graft, a peripheral graft, a venous catheter or an in-dwelling port. In one embodiment, the arteriovenous graft comprises a prosthetic bridge. In other embodiments, the catheter is an indwelling dual lumen catheter and treating the indwelling dual lumen catheter promotes clinical stability sufficient to permit hemodialysis.

In one embodiment, treating the vascular access structure promotes normal or near-normal blood flow through and downstream of the structure. For example, normal or near-normal blood flow is blood flow at a rate sufficient to prevent re-circulation during hemodialysis. According to additional embodiments, treating the vascular access structure promotes normal or near-normal vessel diameter and reduces flow re-circulation during hemodialysis.

In the case of an arteriovenous native fistula, treating the arteriovenous native fistula enhances clinical maturation sufficient to permit hemodialysis, reduces delay in maturation of the arteriovenous native fistula and promotes repetitive cannulation. In the case of an arteriovenous graft, treating the arteriovenous graft promotes clinical stability sufficient to restore normal or near normal circulation. In various of the embodiments, the implantable material reduces the occurrence of revision in a patient having an access structure.

In one embodiment, enhancing maturation is characterized by an ability to repetitively cannulate the fistula for dialysis. According to another embodiment, enhancing maturation is characterized by an ability to obtain sufficient blood flow during dialysis. Preferably, sufficient blood flow comprises a rate of about 350 ml/min. According to various embodiments, application of the biocompatible material to the arteriovenous fistula is preceded by or coincident with administration of a therapeutic agent, physical dilatation or stenting. The arteriovenous fistula is radiocephalic, brachiocephalic, or brachiobasilic.

In one preferred embodiment, the invention is a method for preventing an arteriovenous fistula from failing to mature in a human comprising the step of locating an implantable material comprising a biocompatible matrix and vascular endothelial cells at, adjacent to or in the vicinity of the fistula thereby to prevent a fistula from failing to mature. In one embodiment, failing to mature is characterized by an inability to repetitively cannulate the fistula for dialysis or by an inability to obtain sufficient blood flow during dialysis, wherein the sufficient blood flow comprises a rate of about 350 ml/min. In other embodiments, failing to mature is characterized by an arteriovenous fistula that can not be cannulated at least 2 months, at least 3 months, or at least 4 months after creation.

In another embodiment, the invention is a method of maintaining a blood flow rate of an arteriovenous graft sufficient to permit dialysis comprising the step of providing an implantable material comprising cells and a biocompatible matrix wherein said implantable material is disposed on an exterior surface of said arteriovenous graft at, adjacent or in the vicinity of a prosthetic bridge of a venous outflow region of said arteriovenous graft in an amount effective to maintain blood flow rate of the graft sufficient to permit dialysis. In one embodiment, the blood flow rate at the venous outflow region of said arteriovenous graft is substantially similar to the blood flow rate upstream of said outflow region.

In another embodiment, the invention is a method of maintaining normal blood flow of a peripheral bypass graft sufficient to maintain peripheral circulation comprising the step of providing an implantable material comprising cells and a biocompatible matrix wherein said implantable material is disposed on an exterior surface of said bypass graft at, adjacent or in the vicinity of a prosthetic bridge in an amount effective to maintain blood flow rates of the bypass graft sufficient to maintain peripheral circulation. In one embodiment, an inflow blood rate and an outflow blood rate are substantially similar.

In another embodiment, the invention is a method of maintaining a blood pressure of an arteriovenous graft sufficient to permit dialysis comprising the step of providing an implantable material comprising cells and a biocompatible matrix wherein said implantable material is disposed on an exterior surface of said arteriovenous graft at, adjacent or in the vicinity of a prosthetic bridge of a venous outflow region of said arteriovenous graft in an amount effective to maintain blood pressure sufficient to permit dialysis. In one embodiment, the blood pressure at the venous outflow region of said arteriovenous graft is substantially similar to the blood pressure upstream of said outflow region. The prosthetic bridge is selected from the group consisting of: saphenous vein; bovine heterograft; umbilical vein; dacron; PTFE; ePTFE, polyurethane; bovine mesenteric vein; and cryopreserved femoral vein allograft. According to a preferred embodiment, the prosthetic bridge is ePTFE.

In another embodiment, the invention is a method of promoting tissue integration of a prosthetic bridge of an arteriovenous graft or a peripheral bypass graft comprising the step of providing an implantable material comprising cells and a biocompatible matrix wherein said implantable material is disposed on an exterior surface of said arteriovenous graft or said peripheral bypass graft at, adjacent or in the vicinity of a prosthetic bridge in an amount effective to promote tissue integration of said bridge. In certain embodiments, the implantable material promotes smooth muscle cell proliferation or migration within or in the vicinity of an interior lumen surface of said prosthetic bridge or promotes endothelial cell proliferation or migration within or in the vicinity of an interior lumen surface of said prosthetic bridge. In certain other embodiments, the implantable material promotes smooth muscle cell and/or endothelial cell proliferation at, adjacent or in the vicinity of the graft.

In another embodiment, the invention is a method of preventing or reducing the incidence of dehiscence of an arteriovenous fistula or arteriovenous graft comprising the step of providing an implantable material comprising cells and a biocompatible matrix wherein said implantable material is disposed on an exterior surface of said fistula or arteriovenous graft at, adjacent or in the vicinity of a prosthetic bridge of a venous outflow region of said arteriovenous graft in an amount effective to prevent or reduce the incidence of dehiscence.

According to other embodiments, the providing step is performed as an interventional therapy following failure of a native arteriovenous fistula or following failure of a native or saphenous vein peripheral bypass.

In another aspect, the invention is an implantable material comprising cells and a biocompatible matrix suitable for treating a vascular access structure. The cells are endothelial cells or cells having an endothelial-like phenotype. The biocompatible matrix is a flexible planar form or a flowable composition. In a particularly preferred embodiment, the cells are vascular endothelial cells. The flexible planar form is configured for implantation at, adjacent or in the vicinity of a vascular access structure. In certain embodiments, this form defines a slot. According to one embodiment of the flowable composition, the flowable composition is a shape-retaining composition.

In other embodiments, the invention is an implantable material comprising cells and a biocompatible matrix suitable for use with methods for enhancing maturation of an arteriovenous fistula by preventing an arteriovenous fistula from failing to mature. The cells are endothelial cells or cells having an endothelial-like phenotype and the biocompatible matrix is a flexible planar form or a flowable composition. In one embodiment, the flexible planar form is configured for implantation at, adjacent or in the vicinity of a native fistula. In certain embodiments, this form is configured such that it defines a slot or series of slots. With respect to the flowable composition, it is a shape-retaining composition.

In another embodiment, the invention is an implantable material comprising cells and a biocompatible matrix wherein the implantable material is disposed on an exterior surface of a blood vessel at, adjacent or in the vicinity of a prosthetic bridge. The prosthetic bridge is situated at or near a venous outflow region of an arteriovenous graft or is situated at or near an outflow of In another aspect, the invention is a transport media composition for storing an implantable material comprising a biocompatible matrix and engrafted cells. The transport media composition comprising an amount of VEGF sufficient to maintain cell viability or an inhibitory phenotype and for the cells to remain viable for an extended period of time when stored in said transport media composition at temperatures below the cells' standard cell culture temperature.

In another aspect, the invention is a method for storing an implantable material comprising a biocompatible matrix and engrafted cells for an extended period of time at a temperature below the cells' standard cell culture temperature. The method comprises the steps of bathing the implantable material in a transport media composition comprising an amount of VEGF sufficient to maintain cell viability or an inhibitory phenotype during storage. The cells remain viable for an extended period of time when stored in said transport media composition at a temperature below the cells' standard cell culture temperature.

According to one embodiment, the transport media composition contains an amount of VEGF sufficient to maintain cell viability or an inhibitory phenotype at a temperature below the cells' standard cell culture temperature and greater than the amount of VEGF required at the cells' standard cell culture temperature. According to one embodiment, the amount of VEGF is about 4 ng/mL.

According to additional embodiments, the implantable material is stored in said transport media composition at a temperature below 37° C. or at ambient temperature for an extended period of about 1 week, about 2 weeks, or about 3 weeks. The cells are endothelial cells or endothelial-like cells that are near-confluent, confluent, or post-confluent at the time of storage, and at least 80% viable.

In another aspect, the invention is a cryopreservation media composition for cryopreserving an implantable material comprising a biocompatible matrix and engrafted cells. The cryopreservation media composition comprising a cryopreservative, a polysaccharide and serum. Cell viability or an inhibitory phenotype and matrix integrity are maintained for an extended period of time when stored at at least about −4° C.

In one embodiment, the amount of serum in the cryopreservation media composition exceeds the amount of serum for routine culturing of the cells, for example, 20% serum or 50% serum. In one embodiment, the serum is fetal bovine serum. In one embodiment, the polysaccharide in the cryopreservation media composition exceeds the amount of polysaccharide for routine culturing of the cells, for example at least about 4% polysaccharide or at least about 4.5% polysaccharide. In one embodiment, the polysaccharide is dextran. In another embodiment, the cryopreservation media composition further comprises about 10% DMSO.

According to one embodiment, the cryopreservation media composition is used for storage at at least about −80° C., at least about −140° C., or at at least about −160° C. According to various embodiments, the extended period of time is about 1 month, about 6 months or about 1 year. In one embodiment, cell viability is at least about 80%.

In another aspect, the invention is a cryopreserved implantable material comprising a biocompatible matrix engrafted with cells and a volume of cryopreservation media composition sufficient to maintain cell viability or an inhibitory phenotype and matrix integrity while cryopreserved, wherein the cryopreservation media composition comprises a cryopreservative, a polysaccharide and serum.

In another aspect, the invention is a method of preparing an implantable material comprising a biocompatible matrix and engrafted cells. The method comprises the steps of providing a working cell bank comprising cells, providing a hydrated biocompatible matrix material, seeding the hydrated biocompatible matrix material with cells from the working cell bank, placing the cell seeded biocompatible matrix material in an incubator to facilitate cell attachment, placing the cell seeded biocompatible matrix material in an incubator until the cells are near-confluent, confluent, or post-confluent, and assessing cell count, cell viability and cell functionality of the cell seeded biocompatible matrix material.

In one embodiment, the method further comprises the steps of placing the cell seeded biocompatible matrix material in a vial suitable for cryopreservation, introducing to the near-confluent, confluent, or post-confluent cell seeded biocompatible matrix material a volume of cryopreservation media composition comprising a cryopreservative, a polysaccharide and serum sufficient to preserve cell viability or an inhibitory phenotype and matrix integrity while the material is cryopreserved, placing the vial containing the cell seeded biocompatible matrix material and cryopreservation media composition in a freezing container, introducing an agent which controls the freezing rate to the freezing container, placing the freezing container containing said agentl in a freezer at at least −4° C., removing the freezing container from the at least about −4° C. freezer, and placing the freezing container in a freezer at at least about −80° C.

In another embodiment, the method further comprises the steps of removing the freezing container from the at least −80° C. freezer and placing the freezing container in a freezer at at least −160° C.

In another embodiment, the method further comprises the steps of removing the vial from the freezer, placing the vial in ambient temperature air for about 15 minutes followed by placing the vial in ambient temperature water bath for about 15 minutes, removing the implantable material from the vial, rinsing the implantable material in rinse media composition for about 5 minutes, and placing the implantable material in cell culture media for about 48 hours.

In another embodiment, the method further comprises the steps of removing the vial from the freezer, placing the vial in ambient temperature air for about 15 minutes followed by placing the vial in ambient temperature water bath for about 15 minutes, removing the implantable material from the vial, and rinsing the implantable material in a rinse solution composition for about 30 minutes.

In another embodiment, the method further comprises the steps of placing the cell seeded biocompatible matrix material in a vial suitable for storage and introducing to the near-confluent, confluent, or post-confluent cell seeded biocompatible matrix material a volume of transport media composition comprising an amount of VEGF sufficient to maintain cell viability or an inhibitory phenotype while the material is stored in said composition.

In another embodiment, the method further comprises the steps of preparing the cell seeded biocompatible matrix material for cryopreservation according to a disclosed method or for storage according to a disclosed method, preparing the vial for transport and transporting the outer box to a clinical site for administration to a patient.

In another embodiment, the method further comprises the steps of placing the vial containing the cell seeded biocompatible matrix material into an inner box, placing the inner box into an insulated outer box, and providing product documentation.

In one embodiment of the method, the cell seeded biocompatible matrix material is clinical trial material and the patient is a participant in a clinical trial. In another embodiment of the method, the implantable material is prepared on a commercial scale. In another aspect, the invention is a robotic system to perform any of the disclosed methods.

In another aspect, the invention is a method of manufacturing an implantable material comprising cells and a biocompatible matrix, the method comprising the step of contacting the biocompatible matrix with the cells using reagents and conditions suitable therefore, wherein the cells are in an amount sufficient to populate the matrix and grow to a confluent, near-confluent or post-confluent population and further wherein the matrix is populated with cell typing-independent, non-compatibility tested, non-matched cells. In another aspect, the invention is a method of providing an implantable material manufactured according to this method. In a further aspect, the invention is an implantable material comprising cells and a biocompatible matrix manufactured according to this method.

BRIEF DESCRIPTION OF THE DRAWINGS

In the drawings, like reference characters generally refer to the same parts throughout the different views. Also, the drawings are not necessarily to scale or proportion, emphasis instead generally being placed upon illustrating the principles of the invention.

FIG. 2A is a schematic perspective view of a contoured flexible planar form of implantable material for administration to an exterior surface of a tubular anatomical structure according to an illustrative embodiment of the invention.

FIGS. 2B, 2C, 2D, 2E, 2F and 2G are schematic perspective views of a contoured flexible planar form of the implantable material comprising a slot according to various illustrative embodiments of the invention.

DETAILED DESCRIPTION OF THE INVENTION

Figure 1:
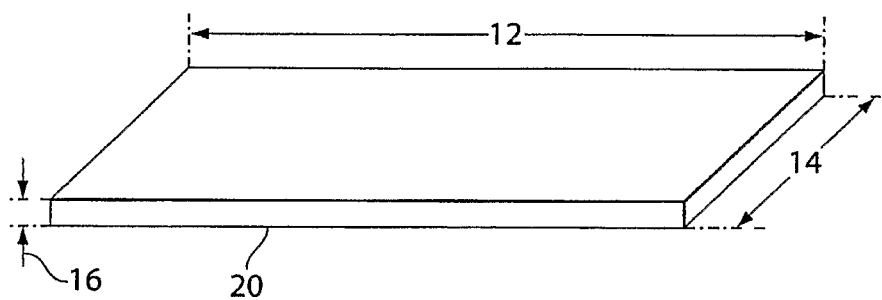
FIG. 1 is a schematic perspective view of a flexible planar form of implantable material for administration to an exterior surface of a tubular anatomical structure according to an illustrative embodiment of the invention.

As explained herein, the invention is based on the discovery that a cell-based therapy can be used to treat vascular access structures. The teachings presented below provide sufficient guidance to make and use the materials and methods of the present invention, and further provide sufficient guidance to identify suitable criteria and subjects for testing, measuring, and monitoring the performance of the materials and methods of the present invention.

Accordingly, a cell-based therapy for clinically managing vascular access complications and/or failures has been developed. An exemplary embodiment of the present invention comprises a biocompatible matrix and cells suitable for use with the treatment paradigms described herein. Specifically, in one preferred embodiment, the implantable material comprises a biocompatible matrix and endothelial cells or endothelial-like cells. In one embodiment, the implantable material is in a flexible planar form and comprises endothelial cells or endothelial-like cells, preferably human aortic endothelial cells and the biocompatible matrix, the product gelatin sponge commonly known as GELFOAM gelatin sponge (Pfizer, New York, N.Y., hereinafter "Gelfoam matrix"). According to another preferred embodiment, the implantable material is in a flowable form and comprises endothelial cells or endothelial-like cells, preferably human aortic endothelial cells and the biocompatible matrix, the product gelatin particles commonly known as GELFOAM gelatin particles or powder (Pfizer, New York, N.Y., hereinafter "Gelfoam particles").

Implantable material of the present invention comprises cells engrafted on, in and/or within a biocompatible matrix. Engrafted means securely attached via cell to cell and/or cell to matrix interactions such that the cells withstand the rigors of the preparatory manipulations disclosed herein. As explained elsewhere herein, an operative embodiment of implantable material comprises a near-confluent, confluent or post-confluent cell population having a preferred phenotype. It is understood that embodiments of implantable material likely shed cells during preparatory manipulations and/or that certain cells are not as securely attached as are other cells. All that is required is that implantable material comprise cells that meet the functional or phenotypical criteria set forth herein.

The implantable material of the present invention was developed on the principals of tissue engineering and represents a novel approach to addressing the above-described clinical needs. The implantable material of the present invention is unique in that the viable cells engrafted on, in and/or within the biocompatible matrix are able to supply to the vascular access structure and associated vasculature multiple cell-based products in physiological proportions under physiological feed-back control. As described elsewhere herein, the cells suitable for use with the implantable material are endothelial or endothelial-like cells. Local delivery of multiple compounds by these cells and physiologically-dynamic dosing provide more effective regulation of the processes responsible for maintaining a functional vascular access structure and diminishing vascular access complications and/or failure. Importantly, the endothelial cells, for example, of the implantable material of the present invention are protected from the erosive blood flow within the vessel lumen because of its placement at a non-luminal surface of the vessel, for example, at the adventitia or contacting an exterior surface of a vessel. The implantable material of the present invention, when wrapped, deposited or otherwise contacted with such an exterior target site, i.e., the anastomosis and/or its surrounds, serves to reestablish homeostasis. That is, the implantable material of the present invention can provide an environment which mimics supportive physiology and is conducive to vascular access structure formation, maturation, integration and/or stabilization.

For purposes of the present invention, contacting means directly or indirectly interacting with an extraluminal or non-luminal surface as defined elsewhere herein. In the case of certain preferred embodiments, actual physical contact is not required for effectiveness. In other embodiments, actual physical contact is preferred. All that is required to practice the present invention is extraluminal or non-luminal deposition of an implantable material at, adjacent or in the vicinity of an injured or diseased site in an amount effective to treat the injured or diseased site. In the case of certain diseases or injuries, a diseased or injured site can clinically manifest on an interior lumen surface. In the case of other diseases or injuries, a diseased or injured site can clinically manifest on an extraluminal or non-luminal surface. In some diseases or injuries, a diseased or injured site can clinically manifest on both an interior lumen surface and an extraluminal or non-luminal surface. The present invention is effective to treat any of the foregoing clinical manifestations.

For example, endothelial cells can release a wide variety of agents that in combination can inhibit or mitigate adverse physiological events associated with acute complications following vascular access structure creation. As exemplified herein, a composition and method of use that recapitulates normal physiology and dosing is useful to enhance vascular access structure formation, maturation, integration and/or stabilization, as well as promote long-term patency of such vascular access structures. Typically, treatment includes placing the implantable material of the present invention at, adjacent or in the vicinity of the vascular access structure site, for example, in the perivascular space external to the lumen of the artery and vein involved in the procedure. When wrapped, wrapped around, deposited, or otherwise contacting an injured, traumatized or diseased blood vessel, the cells of the implantable material can provide growth regulatory compounds to the vasculature, for example to the underlying smooth muscle cells within the blood vessel. It is contemplated that, when situated at an extraluminal site, the cells of the implantable material provide a continuous supply of multiple regulatory compounds which can penetrate vessel tissue and reach the lumen, yet the cells are protected from the adverse mechanical effects of blood flow in the vessel(s). As described herein, one preferred extraluminal site is an exterior surface of a blood vessel.

Treatment with a preferred embodiment of the present invention can encourage normal or near normal healing and normal physiology. On the contrary, in the absence of treatment with a preferred embodiment of the present invention, normal physiological healing is impaired, e.g., native endothelial cells and smooth muscle cells can grow abnormally at an exuberant or uncontrolled rate following creation of a vascular access structure, leading to adverse clinical consequences, including vascular access structure failure. Accordingly, as contemplated herein, treatment with the implantable material of the present invention will improve the healing of native tissue at the anastomotic site(s) to maintain vascular access structure patency.

For purposes of the present invention, vascular access structures may be formed in a variety of configurations. Vascular access structures can include naturally occurring or surgically created arteriovenous fistula, arteriovenous grafts, peripheral bypass grafts, in-dwelling venous catheters, in-dwelling vascular ports, or other vascular anastomotic structures created to improve vascular access in a patient. Additionally, various embodiments of vascular access structures are formed in a variety of configurations including side-to-side, end-to-side, end-to-end and side-to-end anastomoses. Vascular access structures can also be placed in a variety of anatomical locations.

The implantable material of the present invention can be placed in a variety of configurations at the vascular access structure to be treated. According to certain embodiments, the implantable material of the present invention can be placed both at the anastomotic juncture and also placed on the proximal vein segment, distal to the anastomosis. In other embodiments, the implantable material of the present invention can be placed on the arterial segment, on the proximal vein segment, on the distal vein segment, and/or bridging the vascular access structure. In another embodiment, the implantable material also can be placed on the graft material or a portion of the graft material at the anastomotic junction. The vessels can be contacted in whole or in part, for example, the implantable material of the present invention can be applied to the vessels circumferentially or in an arc configuration. A vessel and/or vascular access structure need only be in contact with an amount of implantable material sufficient to improve formation, maturation, integration and/or stabilization of the vascular access structure.

Arteriovenous Fistula. According to certain embodiments, an arteriovenous fistula ("AV fistula") created for vascular access can be treated with the implantable material of the present invention. An AV fistula can be placed in a variety of locations within the patient, including, for example, placement in the neck, wrist, upper arm and lower arm. Clinical AV fistula configurations include radiocephalic (between the radial artery and the cephalic vein), Brescia-Cimino (a side-to-side anastomosis of the radial artery and the cephalic vein within the wrist), brachiocephalic (between the brachial artery and the cephalic vein), brachial-antecubital (between the brachial artery and the antecubital vein), brachiobasilic (a transposed basilic vein), ulnarcephalic (between the ulnar artery and the cephalic vein), and saphenous loop (saphenous vein and the right side of the femoral artery) fistula.

Complications from AV fistula surgery typically occur during three phases. These phases are an acute phase which is often characterized by thrombosis, an intermediate phase whose clinical signature is a failure of the fistula to mature, and finally a more chronic failure of an already-established, functioning fistula which, for example, can be due to progressive venous stenosis.

Characteristics of AV fistula maturation include, for example, the ability to repetitively cannulate the fistula for dialysis. Another characteristic of AV fistula maturation is the ability to obtain sufficient dialysis blood flow useful for hemodialysis. Adequate blood flow is at least a flow rate adequate to support dialysis using a dialysis machine such that recirculation does not occur. A sufficient dialysis blood flow for purposes of the present invention is a blood flow of at least about 350 mL/min at a time point no more than 24 weeks, preferably more than 20 weeks, more preferably 16 weeks, and most preferably twelve weeks after the creation of the fistula. The mechanisms of AV fistula failure to mature are currently understood to include, for example, early thrombosis of the fistula vessels, stenoses at or near the anastomotic site, the presence of accessory veins, including collateral or venous side branches, inadequate vein size, including inadequate vein internal diameter, and late fistula failure due to progressive stenosis. Accessory veins can prevent the development of the fistula by diverting blood flow and by not allowing for the vein associated with the fistula to become of adequate size to allow for cannulation. It is currently thought that accessory veins may develop, for example, in response to the presence of a stenosis in the fistula. The mechanisms of AV fistula maturation are multimodal and generally require assessment of multiple clinical indicia. The absence of stenosis alone is generally an insufficient indication of a mature AV fistula.

Moreover, an AV fistula that is considered adequate for the purpose of dialysis requires both maturation of the fistula, those changes that occur in the vein segment of the fistula which allow the fistula to be repetitively cannulated; and, blood flow sufficient to support dialysis. An AV fistula can remain patent even when there is very little blood flow, but a patent AV fistula may not be clinically adequate for dialysis. For purposes of the present invention, clinically adequate blood flow for dialysis is about 150-500 mL/minute, preferably about 300-500 mL/minute, and most preferably about 350-400 mL/minute; suitable blood pressures are about 50-180 mmHg, preferably about 50-120 mmHg.

For purposes of the present invention, it is believed that treatment with the implantable material of the present invention provides a beneficial homeostatic environment such that complications common in AV fistula maturation, for example, thrombosis, stenosis, clotting and/or the growth of accessory veins are reduced when placed adjacent to or in the vicinity at the fistula whether at the time of fistula creation or at a later stage. This type of beneficial environment allows an AV fistula to proceed to maturation and/or remain in a mature state. For example, maturation is functionally established when the AV fistula vein thickens and is able to conduct high flow, high pressure blood. Treatment of an AV fistula with the implantable material provided for herein enhances maturation of the fistula and/or prevents the fistula from failing to mature. It is understood for purposes of the present invention that enhancement of AV fistula maturation includes any improvement in the functioning of the fistula, including its formation, time required to reach a functional state as well as maintenance of the fistula in a mature form.

Immediate post-operative thrombosis can prevent the formation of a patent AV fistula and lead to early failure of the fistula. As explained herein, treatment with the implantable material of the present invention at the time of surgery can prevent the AV fistula from immediate failure due to post-operative thrombosis. For example, the implantable material releases anti-thrombotic mediators that reduce thrombosis and can maintain a patent fistula through the stages of fistula formation and maturation.

Placement of the implantable material at or in the vicinity of the site of the AV fistula at the time of surgery can also enhance maturation by reducing stenosis at or near the fistula anastomoses, allowing the fistula to become of adequate size to provide sufficient blood flow to support dialysis, facilitating venous and arterial dilatation, decreasing the formation of parasitic accessory veins, maintaining native accessory veins to enhance maturation of the fistula, and improving the size of the vein.

Additionally, an AV fistula requires a longer period of time to reach maturation than an AV graft. During the period of fistula maturation, hemodialysis is generally conducted using a percutaneous or indwelling catheter, leading to an increased risk of infection and compromising central vein patency. Placement of the implantable material at the site of an AV fistula at the time of fistula creation can reduce the time required for fistula maturation, thereby reducing the associated risks of infection and compromised central vein patency. Placement of the implantable material at the site of an indwelling catheter can reduce the risk of thrombosis, intimal hyperplasia and restenosis associated with the indwelling catheter, thereby reducing the associated risks of infection and compromised central vein patency.

Finally, use of the implantable material described herein can decrease late failure of a mature AV fistula. A mature fistula may experience decreased blood flow and increased venous stenosis due to late progressive stenosis. Stenosis or occlusion of a fistula to a degree sufficient to reduce blood flow below a level necessary for dialysis may require interventional angioplasty or stenting of the fistula to restore adequate blood flow levels. Such interventional therapies increase the risk of venous stenosis and occlusion, further preventing the formation of a mature fistula. Furthermore, stenting can result in occlusive thrombosis or restenosis of the treated vessel in the portion of the vessel distal and proximal to the stent, often referred to as edge effects.

Application of the implantable material can result in positive remodeling (a combination of vascular dilatation with a simultaneous inhibition of venous neointimal hyperplasia) thereby preventing late progressive stenosis, increasing blood flow of the mature fistula, reducing the need for rehabilitative angioplasty or stenting of an occluded fistula, preventing stent-associated edge effects, and prolonging the lifetime and usability of the mature fistula.

The implantable material of the present invention can be provided to the fistula at any of a number of distinct stages. For example, treatment at the time of surgery can prevent the AV fistula from failing to mature and/or can enhance maturation of the fistula. The implantable material can also be provided after the initial surgery to hasten healing generally, as well as after a mature AV fistula has formed to maintain it in a clinically stable state. Additionally, the implantable material can also rescue a mature AV fistula that subsequently fails and/or can extend the lifetime of a mature fistula. These situations are non-limiting examples of enhancement of AV fistula maturation. Accordingly, it is contemplated that the implantable material can be used not only at the time of initial surgery to create the AV fistula, but also at subsequent time points (e.g., for maintaining a mature fistula or rescuing a mature fistula from failing). Subsequent administrations can be accomplished surgically or non-invasively.

Arteriovenous Graft. According to additional embodiments, an arteriovenous graft ("AV graft") created for vascular access can be treated with implantable material of the present invention. An AV graft can be in the form of a forearm straight graft, a forearm loop graft or an upper arm graft. Arterial inflow sites include, but are not limited to, the common carotid artery, the radial artery at the wrist, the brachial artery in the antecubital fossa, the brachial artery in the lower portion of the arm, the brachial artery just below the axilla, the axillary artery and the femoral artery. Venous outflow sites include, but are not limited to, the median antecubital vein, the proximal cephalic vein, the distal cephalic vein, the basilic vein at the level of the elbow, the basilic vein at the level of the upper arm, the axillary vein, the jugular vein and the femoral vein. Additional arterial and venous locations suitable for formation of an AV graft include the chest wall (axillary artery to the subclavian vein), the lower extremities (femoral artery/vein, saphenous vein, or tibial (anterior) artery), the aorta to the vena cava, the axillary artery to the femoral vein or the femoral artery to the axillary vein.

For purposes of the present invention, a functional AV graft involving a prosthetic bridge suitable for dialysis is able to conduct high-flow, high-pressure blood through the prosthetic bridge. In such AV grafts, the blood flow rate at the venous outflow region of the graft is substantially similar to the blood flow rate upstream of the graft outflow region. Blood flow rates suitable for dialysis are about 150-500 mL/min, preferably about 300-500 mL/min, and most preferably about 350-400 mL/min; suitable blood pressures are about 50-180 mmHg, preferably about 50-120 mmHg.

AV grafts generally fail due to graft-associated intimal hyperplasia followed by graft-associated thrombosis at the venous-graft anastomosis or at the proximal venous segment. AV grafts are also vulnerable to failure due to poor tissue integration between the native vessels and the prosthetic bridge material and eventual dehiscence of the bridge material from the vessels.

For purposes of the present invention, treatment with the implantable material of the present invention provides a beneficial homeostatic environment such that complications associated with AV graft integration and maturation, for example, thrombosis, stenosis, clotting and/or dehiscence are reduced whether at the time of graft creation or at a later stage. This type of beneficial environment allows the AV graft associated blood vessels to fully integrate with the prosthetic bridge material. For example, maturation is functionally established when the AV graft integrates and is able to conduct high flow, high pressure blood. As demonstrated herein, treatment of an AV graft with implantable material enhances integration and maturation of the graft. For purposes of this invention, it is understood that enhancement of AV graft integration and/or maturation includes any improvement in the functioning of the graft, including its formation, time required to reach a functional state, as well as maintenance of the graft in a functional form.

Immediate post-operative graft-associated thrombosis can prevent tissue integration and eventual formation of a patent AV graft, and can lead to early failure of the graft. As explained herein, treatment at the time of surgery can prevent the AV graft from immediate failure due to post-operative thrombosis. For example, the implantable material releases anti-thrombotic mediators that reduce thrombosis and maintain a patent graft through the stages of graft integration and maturation.

Placement of the implantable material at, adjacent, or in the vicinity of the AV graft anastomosis; at, adjacent, or in the vicinity of the venous outflow region of the graft; and/or at, adjacent, or in the vicinity of the graft at the time of surgery can also enhance integration and maturation by reducing immediate thrombosis and progressive stenosis at or near the graft anastomoses. This therapeutic effect allows the graft sufficient time to become adequately integrated with the prosthetic bridge material, minimizes blood vessel thrombosis and occlusion, and maintains adequate vessel internal diameter to support blood flow sufficient for dialysis.

Administration of the implantable material can also minimize later failure of a mature AV graft. A mature graft can experience decreased blood flow and increased venous stenosis due to late progressive stenosis. Application of the implantable material can result in positive venous remodeling (a combination of vascular dilatation with a simultaneous inhibition of venous neointimal hyperplasia) thereby preventing late progressive stenosis, increasing blood flow of the mature graft and prolonging the lifetime and usability of the mature graft.

As demonstrated herein, treatment of an AV graft anastomosis with the implantable material of the present invention promotes formation of a functional AV graft suitable for dialysis. It is further understood that, for purposes of the present invention, formation of a functional AV graft includes any improvement in the clinical functioning of the graft, or to the process of formation of the graft anastomoses or integration of the prosthetic bridge, and/or maintenance of the graft anastomoses in a mature form, including a reduction in the incidence of dehiscence.

As is well recognized by the clinical practitioner, AV graft adequacy requires that a graft both support and maintain adequate blood flow. In the case of AV grafts useful for hemodialysis, adequate blood flow is at least a flow rate adequate to support dialysis using a dialysis machine such that recirculation does not occur. A clinically failed AV graft is one which can not support blood flow adequate to support dialysis. It is expected that a preferred embodiment of the present invention will delay the onset of, or diminish, AV graft failure by promoting the formation of a functional graft which can support adequate blood flow for dialysis.

Peripheral Bypass Graft. According to additional embodiments, a peripheral graft created to bypass a failing peripheral blood vessel can be treated with the implantable material of the present invention. A peripheral bypass graft can be placed in a variety of anatomical locations, including the extremities such as a region of the leg either above or below the knee. A peripheral bypass graft can be used to bypass a blocked peripheral vessel, including a blockage in a peripheral artery or vein. A peripheral bypass graft can be used to restore and/or maintain normal blood flow to the extremities, for example, a rate of blood flow sufficient to maintain normal or near normal peripheral circulation. According to certain embodiments, the peripheral bypass graft is formed from above the region of blockage to below the region of blockage. In certain embodiments, the present invention can be used to improve the functionality, integration, maturation and/or stabilization of a peripheral bypass having bridge comprising native materials; in certain others, the graft has a prosthetic bridge.

In the case of a peripheral bypass graft, the implantable material can be placed on an exterior surface of the blood vessel at one or both ends of the graft and/or on an exterior surface of the graft material. In certain embodiments, the implantable material can contact the peripheral bypass graft junction at one or both ends. In certain other embodiments, the implant can be placed on an exterior of the blood vessel upstream of the peripheral bypass graft.

Placement of a preferred embodiment of implantable material at or near the inflow or outflow regions of a peripheral bypass graft at the time of surgery can also enhance formation of a functional graft, promote integration and/or prevent dehiscence. For purposes of the present invention, a functional peripheral bypass graft is able to conduct normal blood flow at normal pressures. Normal flow rates for a bypass graft below the knee are about 50-150 mL/min, preferably about 80-100 mL/min; above the knee are about 50-150 mL/min, preferably about 80-100 mL/min; pedal grafts are about 25-30 mL/min. Suitable blood pressures are about 50-180 mmHg, preferably about 50-120 mmHg.

In the case of peripheral bypass grafts treated as described herein, outflow rate is substantially similar to the inflow rate. The present invention restores adequate blood flow to the lower extremities and diminishes symptoms associated with inadequate blood flow to the lower extremities. A preferred embodiment of the present invention delays the onset of, or diminishes, peripheral bypass graft failure by promoting formation of a functional peripheral bypass graft with blood flow sufficient to maintain peripheral circulation.

For purposes of the present invention, any prosthetic bridge material is suitable to create a vascular access structure provided that it supports blood flow rates and pressures required for hemodialysis in the case of AV grafts, and supports blood flow rates and pressures required for peripheral circulation in the case of peripheral bypass grafts. Typically, prosthetic bridges are preferably flexible, compatible with cellular integration, and of the appropriate dimensions to support the required blood flow rates. One preferred embodiment utilizes a PTFE, or an ePTFE, polytetrafluoroethylene bridge; another utilizes Dacron® (E.I. duPont de Nemours and Co.). Prosthetic bridges can also be constructed of modified PTFE materials, polyurethane, carbon coated PTFE, and composite grafts. PTFE grafts can be crafted in a variety of physical configurations, including tapered, stretch, ribbed, smooth, and containing multiple levels of PTFE. Prosthetic grafts can also include distal modifications including venous patches, collars and boots interposed between the artery and the fistula. Additional embodiments include native materials such as saphenous vein grafts, umbilical vein grafts, femoral vein allografts, and biological heterografts, including the bovine carotid and bovine mesenteric vein grafts. Composite grafts comprising any of the foregoing are also contemplated herein. The skilled practitioner will recognize suitable equivalents.

Additionally and importantly, in the case of an AV graft or a peripheral bypass graft, a normal or near normal rate of healing encourages endothelial cells to populate the luminal surfaces of the prosthetic bridge thereby facilitating integration of the graft and associated vasculature. To encourage integration, therapeutic factors provided by the cells of the implantable material diffuse into the vessel walls. In the case of a synthetic graft material, the porosity of the synthetic material can also affect the ability of therapeutic factors to reach cells proliferating on the luminal surface of a synthetic graft.

PTFE Graft. In certain preferred embodiments, a 15-25 cm length of 6-mm internal diameter PTFE tubing is used to form the graft (Atrium Advanta VS Standard Wall PTFE graft, 0.6 mm, Atrium Medical Corp, Hudson, N.H.). PTFE, a particularly preferred graft material, is a flexible polymer that has been shown to be non-thrombogenic when used in surgical procedures. It is contemplated that alternative polymer materials, such as Dacron®, having properties similar to those of PTFE, could also be used as graft materials.

The graft may be cut to a desired length to facilitate accurate placement in a particular patient. The graft may be a forearm loop graft or a straight graft. The ends of the graft may be cut at an angle, with flanges, or in another configuration, sufficient to increase the surface area of the graft ends for suturing or to improve the accommodation of the graft by the particular patient. The ends of the graft may also be roughened or otherwise modified to facilitate cell adhesion. Additionally, the graft material may be coated with gelatin, albumin, or another therapeutic agent.

Finally, providing implantable material to a failing or failed AV graft or peripheral bypass graft can result in rehabilitation of the original graft thereby restoring functionality of the graft. In a related circumstance, a failed native AV fistula can be replaced with an AV graft in combination with the implantable material of the present invention as an interventional therapy.

Vascular Access Catheter. According to certain embodiments, an in-dwelling venous catheter created for vascular access can be treated with implantable material of the present invention. A catheter can be placed in a variety of locations within the patient, including, for example, placement in the neck, the chest, and the groin. For purposes of hemodialysis, a dual-lumen catheter can be implanted as an interim vascular access while a fistula is maturing or a graft is integrating post-surgery.

Vascular access catheters generally prematurely fail due to catheter-associated intimal hyperplasia followed by catheter-associated thrombosis at the venous-catheter anastomosis or at the proximal venous section.

For purposes of the present invention, treatment with the implantable material of the present invention provides a beneficial homeostatic environment such that complications associated with vascular access catheter function, for example, thrombosis, stenosis and/or clotting are reduced at the catheter whether at the time of catheter placement or at a later stage. For purposes of this invention, it is understood that enhancement of vascular access catheter function includes any improvement in the functioning of the catheter, or to the maintenance of the catheter in a functional form.

Vascular Access Port. According to certain embodiments, an in-dwelling port created for vascular access can be treated with the implantable material of the present invention. A port can be placed in a variety of locations within the patient, including, for example, placement at a venous or arterial location in the arm, chest, and the groin.

Vascular access ports generally prematurely fail due to port-associated intimal hyperplasia followed by port-associated thrombosis at the venous-port anastomosis or at the proximal venous section.

For purposes of the present invention, treatment with the implantable material of the present invention provides a beneficial homeostatic environment such that complications associated with vascular access port function, for example, thrombosis, stenosis and/or clotting are reduced at the port whether at the time of port placement or at a later stage. For purposes of this invention, it is understood that enhancement of vascular access port function includes any improvement in the functioning of the port, or to the maintenance of the port in a functional form.

General Considerations. In certain embodiments of the invention, additional therapeutic agents are administered prior to, coincident with and/or following administration of the implantable material. For example, agents which prevent or diminish blood clot formation, platelet aggregation or other similar blockages can be administered. Exemplary agents include, for example, heparan sulfate and TGF-β. Other cytokines or growth factors can also be incorporated into the implantable material, depending on the clinical indication necessitating the implant, including VEGF to promote reendothelialization and b-FGF to promote graft integration. Other types of therapeutic agents include, but are not limited to, antiproliferative agents and antineoplastic agents.

Examples include rapamycin, paclitaxel and E2F Decoy agent. Any of the foregoing can be administered locally or systemically; if locally, certain agents can be contained within the implantable material or contributed by the cells.

Additionally, agents which mediate positive tissue remodeling can also be administered in combination with the implantable material embodiments described herein. For example, certain agents can promote normal or normal-like lumen regeneration or remodeling of luminal tissue at a site of vascular injury, including surgical sites. Again, such agents can be contained within the implantable material or contributed by the cells.

As is well recognized by the clinical practitioner, vascular access adequacy for hemodialysis requires vascular access structure maturation and a sufficient blood flow. As explained elsewhere herein, maturation relates to anatomical changes that occur in the vein which permit repeated cannulation during dialysis. Certain of the changes which permit repetitive cannulation relate to vessel size and/or vessel wall thickening and/or lumen diameter. And, also explained herein, certain of these changes permit a blood flow rate adequate to support dialysis. Moreover, as explained elsewhere herein, a clinically failed vascular access structure is one which can not be repetitively cannulated for dialysis and one which can not support blood flow adequate to support dialysis. These clinical failures can be directly correlated with dysfunction in the anatomic parameters described above.

Accordingly, the present invention also provides for methods of accomplishing vascular access-related clinical endpoints including improving cannulation frequency, improving vascular access structure blood flow, promoting vessel wall thickness, maintaining lumen diameter, and/or a combination of the foregoing, wherein the method comprises the step of locating the implantable material at, adjacent or in the vicinity of the vascular access structure in an amount effective to accomplish one or more of the foregoing endpoints.

Furthermore, the present invention also provides methods for identifying successfully maturing vascular access structures, wherein the method comprises the step of monitoring any one of the following clinical parameters: repeated cannulation; blood flow adequate to prevent recirculation during dialysis; vessel wall thickening; lumen diameter adequate to permit blood flow during dialysis, wherein a successfully maturing vascular access structure exhibits at least one of the foregoing parameters.

The implantable material of the present invention can be applied to any tubular anatomical structure requiring interventional therapy to maintain homeostasis. Tubular anatomical structures include structures of the vascular system, the reproductive system, the genitourinary system, the gastrointestinal system, the pulmonary system, the respiratory system and the ventricular system of the brain and spinal cord. As contemplated herein, tubular anatomical structures are those having an interior luminal surface and an extraluminal surface. For purposes of the present invention, an extraluminal surface can be but is not limited to an exterior surface of a tubular structure. In certain structures, the interior luminal surface is an endothelial cell layer; in certain other structures, the interior luminal surface is a non-endothelial cell layer.

Cell Source. As described herein, the implantable material of the present invention comprises cells. Cells can be allogeneic, xenogeneic or autologous. In certain embodiments, a source of living cells can be derived from a suitable donor. In certain other embodiments, a source of cells can be derived from a cadaver or from a cell bank.

In one currently preferred embodiment, cells are endothelial cells. In a particularly preferred embodiment, such endothelial cells are obtained from vascular tissue, preferably but not limited to arterial tissue. As exemplified below, one type of vascular endothelial cell suitable for use is an aortic endothelial cell. Another type of vascular endothelial cell suitable for use is umbilical cord vein endothelial cells. And, another type of vascular endothelial cell suitable for use is coronary artery endothelial cells. Yet other types of vascular endothelial cells suitable for use with the present invention include pulmonary artery endothelial cells and iliac artery endothelial cells.

In another currently preferred embodiment, suitable endothelial cells can be obtained from non-vascular tissue. Non-vascular tissue can be derived from any tubular anatomical structure as described elsewhere herein or can be derived from any non-vascular tissue or organ.

In yet another embodiment, endothelial cells can be derived from endothelial progenitor cells or stem cells; in still another embodiment, endothelial cells can be derived from progenitor cells or stem cells generally. In other preferred embodiments, cells can be non-endothelial cells that are allogeneic, xenogeneic or autologous derived from vascular or non-vascular tissue or organ. The present invention also contemplates any of the foregoing which are genetically altered, modified or engineered.

In a further embodiment, two or more types of cells are co-cultured to prepare the present composition. For example, a first cell can be introduced into the biocompatible implantable material and cultured until confluent. The first cell type can include, for example, smooth muscle cells, fibroblasts, stem cells, endothelial progenitor cells, a combination of smooth muscle cells and fibroblasts, any other desired cell type or a combination of desired cell types suitable to create an environment conducive to endothelial cell growth. Once the first cell type has reached confluence, a second cell type is seeded on top of the first confluent cell type in, on or within the biocompatible matrix and cultured until both the first cell type and second cell type have reached confluence. The second cell type may include, for example, endothelial cells or any other desired cell type or combination of cell types. It is contemplated that the first and second cell types can be introduced step wise, or as a single mixture. It is also contemplated that cell density can be modified to alter the ratio of smooth muscle cells to endothelial cells.

To prevent over-proliferation of smooth muscle cells or another cell type prone to excessive proliferation, the culture procedure can be modified. For example, following confluence of the first cell type, the culture can be coated with an attachment factor suitable for the second cell type prior to introduction of the second cell type. Exemplary attachment factors include coating the culture with gelatin to improve attachment of endothelial cells. According to another embodiment, heparin can be added to the culture media during culture of the second cell type to reduce the proliferation of the first cell type and to optimize the desired first cell type to second cell type ratio. For example, after an initial growth of smooth muscle cells, heparin can be administered to control smooth muscle cell growth to achieve a greater ratio of endothelial cells to smooth muscle cells.

In a preferred embodiment, a co-culture is created by first seeding a biocompatible implantable material with smooth muscle cells to create vessel structures. Once the smooth muscle cells have reached confluence, endothelial cells are seeded on top of the cultured smooth muscle cells on the implantable material to create a simulated blood vessel. This embodiment can be administered, for example, to an AV graft or peripheral bypass graft according to methods described herein to promote the integration of the prosthetic graft material.

All that is required of the cells of the present composition is that they exhibit one or more preferred phenotypes or functional properties. As described earlier herein, the present invention is based on the discovery that a cell having a readily identifiable phenotype when associated with a preferred matrix (described elsewhere herein) can facilitate, restore and/or otherwise modulate vascular endothelial cell physiology and/or luminal homeostasis associated with treatment of vascular access structures such as arteriovenous fistula or arteriovenous graft.

For purposes of the present invention, one such preferred, readily identifiable phenotype typical of cells of the present invention is an ability to inhibit or otherwise interfere with vascular smooth muscle cell proliferation as measured by the in vitro assays described below. This is referred to herein as the inhibitory phenotype.

Another readily identifiable phenotype exhibited by cells of the present composition is that they are anti-thrombotic or are able to inhibit platelet adhesion and aggregation. Anti-thrombotic activity can be determined using an in vitro heparan sulfate assay and/or an in vitro platelet aggregation assay described below.

In a typical operative embodiment of the present invention, cells need not exhibit more than one of the foregoing phenotypes. In certain embodiments, cells can exhibit more than one of the foregoing phenotypes.

While the foregoing phenotypes each typify a functional endothelial cell, such as but not limited to a vascular endothelial cell, a non-endothelial cell exhibiting such a phenotype(s) is considered endothelial-like for purposes of the present invention and thus suitable for use with the present invention. Cells that are endothelial-like are also referred to herein as functional analogs of endothelial cells; or functional mimics of endothelial cells. Thus, by way of example only, cells suitable for use with the materials and methods disclosed herein also include stem cells or progenitor cells that give rise to endothelial-like cells; cells that are non-endothelial cells in origin yet perform functionally like an endothelial cell using the parameters set forth herein; cells of any origin which are engineered or otherwise modified to have endothelial-like functionality using the parameters set forth herein.

Typically, cells of the present invention exhibit one or more of the aforementioned phenotypes when present in confluent, near-confluent or post-confluent populations and associated with a preferred biocompatible matrix such as those described elsewhere herein. As will be appreciated by one of ordinary skill in the art, confluent, near-confluent or post-confluent populations of cells are identifiable readily by a variety of techniques, the most common and widely-accepted of which is direct microscopic examination. Others include evaluation of cell number per surface area using standard cell counting techniques such as but not limited to a hemacytometer or coulter counter.

Additionally, for purposes of the present invention, endothelial-like cells include but are not limited to cells which emulate or mimic functionally and phenotypcially confluent, near-confluent or post-confluent endothelial cells as measured by the parameters set forth herein.

Thus, using the detailed description and guidance set forth below, the practitioner of ordinary skill in the art will appreciate how to make, use, test and identify operative embodiments of the implantable material disclosed herein. That is, the teachings provided herein disclose all that is necessary to make and use the present invention's implantable materials.

And further, the teachings provided herein disclose all that is necessary to identify, make and use operatively equivalent cell-containing compositions. At bottom, all that is required is that equivalent cell-containing compositions are effective to treat vascular access structures in accordance with the methods disclosed herein. As will be appreciated by the skilled practitioner, equivalent embodiments of the present composition can be identified using only routine experimentation together with the teachings provided herein.

In certain preferred embodiments, endothelial cells used in the implantable material of the present invention are isolated from the aorta of human cadaver donors. Each lot of cells is derived from a single or multiple donors, tested extensively for endothelial cell purity, biological function, the presence of bacteria, fungi, known human pathogens and other adventitious agents. The cells are cryopreserved and banked using well-known techniques for later expansion in culture for subsequent formulation in biocompatible implantable materials.

Cell Preparation. As stated above, suitable cells can be obtained from a variety of tissue types and cell types. In certain preferred embodiments, human aortic endothelial cells used in the implantable material are isolated from the aorta of cadaver donors. In other embodiments, porcine aortic endothelial cells (Cell Applications, San Diego, Calif.) are isolated from normal porcine aorta by a similar procedure used to isolate human aortic endothelial cells. Each lot of cells is derived from a single or multiple donors, tested extensively for endothelial cell viability, purity, biological function, the presence of mycoplasma, bacteria, fungi, yeast, known human pathogens and other adventitious agents. The cells are further expanded, characterized and cryopreserved to form a working cell bank at the third to sixth passage using well-known techniques for later expansion in culture and for subsequent formulation in biocompatible implantable material.

The human or porcine aortic endothelial cells are prepared in T-75 flasks pre-treated by the addition of approximately 15 ml of endothelial cell growth media per flask. Human aortic endothelial cells are prepared in Endothelial Growth Media (EGM-2, Cambrex Biosciences, East Rutherford, N.J.). EGM-2 consists of Endothelial Cell Basal Media (EBM-2, Cambrex Biosciences) supplemented with EGM-2 singlequots, which contain 2% FBS. Porcine cells are prepared in EBM-2 supplemented with 5% FBS and 50 µg/ml gentamicin. The flasks are placed in an incubator maintained at approximately 37° C. and 5% $CO_2$/95% air, 90% humidity for a minimum of 30 minutes. One or two vials of the cells are removed from the −160° C.-140° C. freezer and thawed at approximately 37° C. Each vial of thawed cells is seeded into two T-75 flasks at a density of approximately $3\times10^3$ cells per $cm^3$, preferably, but no less than $1.0\times10^3$ and no more than $7.0\times10^3$; and the flasks containing the cells are returned to the incubator. After about 8-24 hours, the spent media is removed and replaced with fresh media. The media is changed every two to three days, thereafter, until the cells reach approximately 85-100% confluence preferably, but no less than 60% and no more than 100%. When the implantable material is intended for clinical application, only antibiotic-free media is used in the post-thaw culture of human aortic endothelial cells and manufacture of the implantable material of the present invention.

The endothelial cell growth media is then removed, and the monolayer of cells is rinsed with 10 ml of HEPES buffered saline (HEPES). The HEPES is removed, and 2 ml of trypsin is added to detach the cells from the surface of the T-75 flask. Once detachment has occurred, 3 ml of trypsin neutralizing solution (TNS) is added to stop the enzymatic reaction. An additional 5 ml of HEPES is added, and the cells are enumerated using a hemocytometer. The cell suspension is centrifuged and adjusted to a density of, in the case of human cells, approximately $1.75 \times 10^6$ cells/ml using EGM-2 without antibiotics, or in the case of porcine cells, approximately $1.50 \times 10^6$ cells/ml using EBM-2 supplemented with 5% PBS and 50 µg/ml gentamicin.

Biocompatible Matrix. According to the present invention, the implantable material comprises a biocompatible matrix. The matrix is permissive for cell growth and attachment to, on or within the matrix. The matrix is flexible and conformable. The matrix can be a solid, a semi-solid or flowable porous composition. For purposes of the present invention, flowable composition means a composition susceptible to administration using an injection or injection-type delivery device such as, but not limited to, a needle, a syringe or a catheter. Other delivery devices which employ extrusion, ejection or expulsion are also contemplated herein. Porous matrices are preferred. A preferred flowable composition is shape-retaining. The matrix also can be in the form of a flexible planar form. The matrix also can be in the form of a gel, a foam, a suspension, a particle, a microcarrier, a microcapsule, or a fibrous structure. A currently preferred matrix has a particulate form.

The matrix, when implanted on an exterior surface of a blood vessel for example, can reside at the implantation site for at least about 56-84 days, preferably about at least 7 days, more preferably about at least 14 days, most preferably about at least 28 days before it bioerodes.

One preferred matrix is the product gelatin sponge commonly known as GELFOAM gelatin sponge (Pfizer, New York, N.Y.), an absorbable gelatin sponge (hereinafter "Gelfoam matrix"). Gelfoam matrix is a porous and flexible surgical sponge prepared from a specially treated, purified porcine dermal gelatin solution.

According to another embodiment, the biocompatible matrix material can be a modified matrix material. Modifications to the matrix material can be selected to optimize and/or to control function of the cells, including the cells' phenotype (e.g., the inhibitory phenotype) as described above, when the cells are associated with the matrix. According to one embodiment, modifications to the matrix material include coating the matrix with attachment factors or adhesion peptides that enhance the ability of the cells to inhibit smooth muscle cell proliferation, to decrease inflammation, to increase heparan sulfate production, to increase prostacyclin production, and/or to increase TGF-$\beta_1$ production. Exemplary attachment factors include, for example, fibronectin, fibrin gel, and covalently attached cell adhesion ligands (including for example RGD) utilizing standard aqueous carbodiimide chemistry. Additional cell adhesion ligands include peptides having cell adhesion recognition sequences, including but not limited to: RGDY, REDVY, GRGDF, GPDSGR, GRGDY and REDV.

According to another embodiment, the matrix is a matrix other than Gelfoam. Additional exemplary matrix materials include, for example, fibrin gel, alginate, polystyrene sodium sulfonate microcarriers, collagen coated dextran microcarriers, PLA/PGA and pHEMA/MMA copolymers (with polymer ratios ranging from 1-100% for each copolymer). According to a preferred embodiment, these additional matrices are modified to include attachment factors or adhesion peptides, as recited and described above. Exemplary attachment factors include, for example, gelatin, collagen, fibronectin, fibrin gel, and covalently attached cell adhesion ligands (including RGD) utilizing standard aqueous carbodiimide chemistry. Additional cell adhesion ligands include peptides having cell adhesion recognition sequences, including but not limited to: RGDY, REDVY, GRGDF, GPDSGR, GRGDY and REDV.

According to another embodiment, the biocompatible matrix material is physically modified to improve cell attachment to the matrix. According to one embodiment, the matrix is cross linked to enhance its mechanical properties and to improve its cell attachment and growth properties. According to a preferred embodiment, an alginate matrix is first cross linked using calcium sulfate followed by a second cross linking step using calcium chloride and routine protocols.

According to yet another embodiment, the pore size of the biocompatible matrix is modified. A preferred matrix pore size is about 25 µm to about 100 µm; preferably about 25 µm to 50 µm; more preferably about 50 µm to 75 µm; even more preferably about 75 µm to 100 µm. Other preferred pore sizes include pore sizes below about 25 µm and above about 100 µm. According to one embodiment, the pore size is modified using a salt leaching technique. Sodium chloride is mixed in a solution of the matrix material and a solvent, the solution is poured into a mold, and the solvent is allowed to evaporate. The matrix/salt block is then immersed in water and the salt leached out leaving a porous structure. The solvent is chosen so that the matrix is in the solution but the salt is not. One exemplary solution includes PLA and methylene chloride.

According to an alternative embodiment, carbon dioxide gas bubbles are incorporated into a non-solid form of the matrix and then stabilized with an appropriate surfactant. The gas bubbles are subsequently removed using a vacuum, leaving a porous structure.

According to another embodiment, a freeze-drying technique is employed to control the pore size of the matrix, using the freezing rate of the ice microparticles to form pores of different sizes. For example, a gelatin solution of about 0.1-2% porcine or bovine gelatin can be poured into a mold or dish and pre-frozen at a variety of different temperatures and then lyophilized for a period of time. The material can then be cross-linked by using, preferably, ultraviolet light (254 nm) or by adding gluteraldehyde (formaldehyde). Variations in pre-freezing temperature (for example −20° C., −80° C. or −180° C.), lyophilizing temperature (freeze dry at about −50° C.), and gelatin concentration (0.1% to 2.0%; pore size is generally inversely proportional to the concentration of gelatin in the solution) can all affect the resulting pore size of the matrix material and can be modified to create a preferred material. The skilled artisan will appreciate that a suitable pore size is that which promotes and sustains optimal cell populations having the phenotypes described elsewhere herein.

Flexible Planar Form. As taught herein, planar forms of biocompatible matrix can be configured in a variety of shapes and sizes, preferably a shape and size which is adapted for implantation at, adjacent or in the vicinity of a fistula, graft, peripheral graft, or other vascular access structure and its surrounds and which can conform to the contoured surfaces of the access structure and its associated blood vessels. According to a preferred embodiment, a single piece of matrix is sized and configured for application to the specific vascular access structure to be treated.

According to one embodiment, the biocompatible matrix is configured as a flexible planar form. An exemplary embodiment configured for administration to a tubular structure such as but not limited to a blood vessel or for administration to a vascular access structure such as but not limited to a vascular anastomosis is illustrated in FIG. 1. Features of length, width, thickness and surface area are not depicted to scale or in a proportionate manner in FIG. 1; FIG. 1 is a non-limiting illustrative embodiment.

With reference to FIG. 1, a flexible planar form 20 is formed from a piece of suitable biocompatible matrix. All that is required is that the flexible planar form 20 be flexible, conformable and/or adaptable to a contoured exterior surface of a tubular structure such as a blood vessel. The flexible planar form 20 can contact an exterior surface of a blood vessel, can wrap an exterior surface or can wrap around an exterior surface.

According to one exemplary embodiment illustrated in FIG. 2A, contoured flexible planar form 20' can be configured to contain definable regions such as a body 30, connected to a bridge 50, connected to a tab 40. The Tab 40 is separable from the body 30 by the bridge 50, although the several regions form a contiguous whole. According to one exemplary embodiment, interior edges of these several regions are arranged to define an interior slot 60 in the contoured flexible planar form 20'. According to a preferred embodiment, these several regions defining the interior slot 60 further define a first termination point 62 within the interior of the contoured flexible planar form 20', a second termination point 64 on an exterior edge of the contoured flexible planar form 20', and a width 66. In this particular exemplary embodiment, the first termination point 62 is at a boundary between the tab 40 and the bridge 50; and the second termination point 64 is at a boundary between the tab 40 and the body 30.

In certain embodiments, it is contemplated that the width 66 of the slot 60 defined by the above-described tab 40, body 30 and bridge 50 is preferably about 0.01 to about 0.04, more preferably about 0.05 to about 0.08, most preferably about 0.06 inches. Preferably, width 66 of slot 60 of flexible planar form 20' is of sufficient dimension to discourage engrafted cells from forming an uninterrupted confluent layer or cell bridge across the width 66 of the slot 60. It is contemplated, however, that embodiments defining a slot 60 and a slot width 66 can be used as described herein even if cells span width 66 by simply cutting or otherwise interrupting such a cell layer or cell bridge.

The current invention further contemplates that the flexible planar form 20' of FIG. 1 can be adapted to define a slot 60 immediately prior to use simply by instructing the skilled practitioner to use a scalpel or other cutting tool to sever the planar form, in part, thereby defining a slot.

In part, the invention disclosed herein is based on the discovery that a contoured and/or conformable flexible planar form allows the implantable material to be applied optimally to a tubular structure without compromising the integrity of the implant or the cells engrafted thereto. One preferred embodiment optimizes contact with and conforms to the anatomy of a surgically-treated vessel and controls the extent of overlap of implantable material. Excessive overlap of implantable material within the adventitial space can cause pressure points on the treated vessel, potentially restricting blood flow through the vessel or creating other disruptions that could delay and/or inhibit homeostasis and normal healing. The skilled practitioner will recognize excessive overlap at the time of implantation and will recognize the need to reposition or alter, e.g., trim, the implantable material. Additionally, in other embodiments, overlap of implantable material can result in over-dosing of therapeutic agents dispersed within the implantable material. As described elsewhere herein, chemicals or other exogenously supplied therapeutic agents can be optionally added to an implant. In certain other embodiments, such agents can be added to a biocompatible matrix and administered in the absence of cells; a biocompatible matrix used in this manner optionally defines a slot.

In contrast, implantable material that does not adequately contact the target tubular structure can lead to insufficient exposure to the clinical benefits provided by the engrafted cells or an under-dosing of therapeutic agent added to the implantable material. The skilled practitioner will recognize that sub-optimal contact at the time of implantation necessitates re-positioning and/or additional implantable material.

Flowable Composition. In certain embodiments contemplated herein, the implantable material of the present invention is a flowable composition comprising a particulate biocompatible matrix. Any non-solid flowable composition for use with an injectable-type delivery device capable of either intraluminal (endovascular) administration by navigating the interior length of a blood vessel or by percutaneous local administration is contemplated herein. The flowable composition is preferably a shape-retaining composition. Thus, an implantable material comprising cells in, on or within a flowable-type particulate matrix as contemplated herein can be formulated for use with any injectable delivery device ranging in internal diameter from about 22 gauge to about 26 gauge and capable of delivering about 50 mg of flowable composition comprising particulate material containing preferably about 1 million cells in about 1 to about 3 ml.

According to a currently preferred embodiment, the flowable composition comprises a biocompatible particulate matrix such as Gelfoam particles, the product gelatin powder commonly known as GELFOAM powder, or the product pulverized gelatin commonly known as pulverized GELFOAM (Pfizer Inc., New York, N.Y.) (hereinafter "Gelfoam particles"), a product derived from porcine dermal gelatin. According to another embodiment, the particulate matrix is Cytodex-3 (Amersham Biosciences, Piscataway, N.J.) microcarriers, comprised of denatured collagen coupled to a matrix of cross-linked dextran.

According to alternative embodiments, the biocompatible implantable particulate matrix is a modified biocompatible matrix. Modifications include those described above for an implantable matrix material.

Examples of flowable compositions suitable for use in this manner are disclosed in co-pending application PCT/US05/44090 filed on Dec. 6, 2005, the entire contents of which is herein incorporated by reference; and, co-pending application PCT/US05/43844 filed on Dec. 6, 2005, the entire contents of which are herein incorporated by reference.

Cell Seeding of Biocompatible Matrix. Pre-cut pieces of a suitable biocompatible matrix or an aliquot of suitable biocompatible flowable matrix are re-hydrated by the addition of EGM-2 without antibiotics at approximately 37° C. and 5% CO2/95% air for 12 to 24 hours. The implantable material is then removed from their re-hydration containers and placed in individual tissue culture dishes. Biocompatible matrix is seeded at a preferred density of approximately 1.5-2.0×105 cells (1.25-1.66×105 cells /cm of matrix) and placed in an incubator maintained at approximately 37° C. and 5% CO2/95% air, 90% humidity for 3-4hours to facilitate cell attachment. The seeded matrix is then placed into individual containers (American Master Tech, Lodi, Calif.) tubes, each fitted with a cap containing a 0.2 μm filter with EGM-2 and incubated at approximately 37° C. and 5% CO2/95% air. The media is changed every two to three days, thereafter, until the cells have reached confluence. The cells in one preferred embodiment are preferably passage 6, but cells of fewer or more passages can be used. Further implantable material preparation protocols according to additional embodiments of the invention are disclosed in co-pending application PCT/US05/43844 filed on Dec. 6, 2005, the entire contents of which are herein incorporated by reference.

Figure 3A:
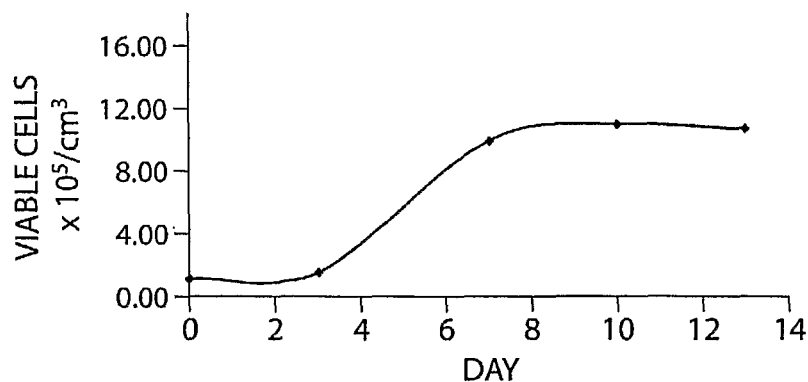
FIGS. 3A and 3B are representative cell growth curves according to an illustrative embodiment of the invention.
Figure 3B:
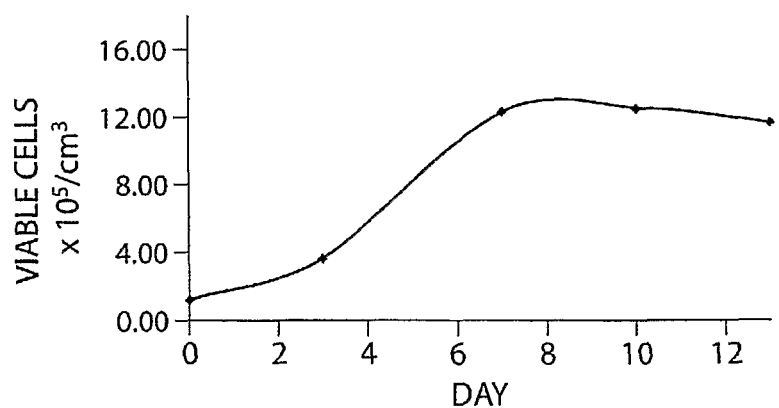

Cell Growth Curve and Confluence. A sample of implantable material is removed on or around days 3 or 4, 6 or 7, 9 or 10, and 12 or 13, the cells are counted and assessed for viability, and a growth curve is constructed and evaluated in order to assess the growth characteristics and to determine whether confluence, near-confluence or post-confluence has been achieved. Representative growth curves from two preparations of implantable material comprising porcine aortic endothelial cell implanted lots are presented in FIGS. 3A and 3B. In these examples, the implantable material is in a flexible planar form. Generally, one of ordinary skill will appreciate the indicia of acceptable cell growth at early, mid- and late time points, such as observation of an increase in cell number at the early time points (when referring to FIG. 3A, between about days 2-6), followed by a near confluent phase (when referring to FIG. 3A, between about days 6-8), followed by a plateau in cell number once the cells have reached confluence (when referring to FIG. 3A, between about days 8-10) and maintenance of the cell number when the cells are post-confluent (when referring to FIG. 3A, between about days 10-14). For purposes of the present invention, cell populations which are in a plateau for at least 72 hours are preferred.

Cell counts are achieved by complete digestion of the aliquot of implantable material with a solution of 0.8 mg/ml collagenase in a trypsin-EDTA solution. After measuring the volume of the digested implantable material, a known volume of the cell suspension is diluted with 0.4% trypan blue (4:1 cells to trypan blue) and viability assessed by trypan blue exclusion. Viable, non-viable and total cells are enumerated using a hemacytometer. Growth curves are constructed by plotting the number of viable cells versus the number of days in culture. Cells are shipped and implanted after reaching confluence.

For purposes of the present invention, confluence is defined as the presence of at least about $4 \times 10^5$ cells/cm$^3$ when in a flexible planar form of the implantable material (1.0×4.0×0.3 cm), and preferably about $7 \times 10^5$ to $1 \times 10^6$ total cells per aliquot (50-70 mg) when in the flexible composition. For both, cell viability is at least about 90% preferably but no less than 80%. If the cells are not confluent by day 12 or 13, the media is changed, and incubation is continued for an additional day. This process is continued until confluence is achieved or until 14 days post-seeding. On day 14, if the cells are not confluent, the lot is discarded. If the cells are determined to be confluent after performing in-process checks, a final media change is performed. This final media change is performed using EGM-2 without phenol red and without antibiotics. Immediately following the media change, the tubes are fitted with sterile plug seal caps for shipping.

Evaluation of Functionality. For purposes of the invention described herein, the implantable material is further tested for indicia of functionality prior to implantation. For example, conditioned media are collected during the culture period to ascertain levels of heparan sulfate, transforming growth factor-$\beta_1$ (TGF-$\beta_1$), basic fibroblast growth factor (b-FGF), and nitric oxide which are produced by the cultured endothelial cells. In certain preferred embodiments, the implantable material can be used for the purposes described herein when total cell number is at least about 2, preferably at least about $4 \times 10^5$ cells/cm$^3$ of flexible planar form; percentage of viable cells is at least about 80-90%, preferably ≥90%, most preferably at least about 90%; heparan sulfate in conditioned media is at least about 0.5-1.0, preferably at least about 1.0 microg/ $10^6$ cell/day. TGF-$\beta_1$ in conditioned media is at least about 200-300, preferably at least about 300 picog/ml/day; b-FGF in conditioned media is below about 200 picog/ml, preferably no more than about 400 picog/ml.

Heparan sulfate levels can be quantitated using a routine dimethylmethylene blue-chondroitinase ABC digestion spectrophotometric assay. Total sulfated glycosaminoglycan (GAG) levels are determined using a dimethylmethylene blue (DMB) dye binding assay in which unknown samples are compared to a standard curve generated using known quantities of purified chondroitin sulfate diluted in collection media. Additional samples of conditioned medium are mixed with chondroitinase ABC to digest chondroitin and dermatan sulfates prior to the addition of the DMB color reagent. All absorbances are determined at the maximum wavelength absorbance of the DMB dye mixed with the GAG standard, generally around 515-525 nm. The concentration of heparan sulfate per $10^6$ cells per day is calculated by subtracting the concentration of chondroitin and dermatan sulfate from the total sulfated glycosaminoglycan concentration in conditioned medium samples. Chondroitinase ABC activity is confirmed by digesting a sample of purified chondroitin sulfate. Conditioned medium samples are corrected appropriately if less than 100% of the purified chondroitin sulfate is digested. Heparan sulfate levels may also be quantitated using an ELISA assay employing monoclonal antibodies.

TGF-$\beta_1$ and b-FGF levels can be quantitated using an ELISA assay employing monoclonal or polyclonal antibodies, preferably polyclonal. Control collection media can also be quantitated using an ELISA assay and the samples corrected appropriately for TGF-$\beta_1$ and b-FGF levels present in control media.

Nitric oxide (NO) levels can be quantitated using a standard Griess Reaction assay. The transient and volatile nature of nitric oxide makes it unsuitable for most detection methods. However, two stable breakdown products of nitric oxide, nitrate ($NO_3$) and nitrite ($NO_2$), can be detected using routine photometric methods. The Griess Reaction assay enzymatically converts nitrate to nitrite in the presence of nitrate reductase. Nitrite is detected colorimetrically as a colored azo dye product, absorbing visible light in the range of about 540 nm. The level of nitric oxide present in the system is determined by converting all nitrate into nitrite, determining the total concentration of nitrite in the unknown samples, and then comparing the resulting concentration of nitrite to a standard curve generated using known quantities of nitrate converted to nitrite.

The earlier-described preferred inhibitory phenotype is assessed using the quantitative heparan sulfate, TGF-$\beta_1$, NO and/or b-FGF assays described above, as well as quantitative in vitro assays of smooth muscle cell growth and inhibition of thrombosis as follows. For purposes of the present invention, implantable material is ready for implantation when one or more of these alternative in vitro assays confirm that the implantable material is exhibiting the preferred inhibitory phenotype.

To evaluate inhibition of smooth muscle cell growth in vitro, the magnitude of inhibition associated with cultured endothelial cells is determined. Porcine or human aortic smooth muscle cells are sparsely seeded in 24 well tissue culture plates in smooth muscle cells growth medium (SmGM-2, Cambrex BioScience). The cells are allowed to attach for 24 hours. The medium is then replaced with smooth muscle cell basal media (SmBM) containing 0.2% FBS for 48-72 hours to growth arrest the cells. Conditioned media is prepared from post-confluent endothelial cell cultures, diluted 1:1 with 2×SMC growth media and added to the cultures. A positive control for inhibition of smooth muscle cell growth is included in each assay. After three to four days, the number of cells in each sample is enumerated using a Coulter Counter. The effect of conditioned media on smooth muscle cell proliferation is determined by comparing the number of smooth muscle cells per well immediately before the addition of conditioned medium with that after three to four days of exposure to conditioned medium, and to control media (standard growth media with and without the addition of growth factors). The magnitude of inhibition associated with the conditioned media samples are compared to the magnitude of inhibition associated with the positive control. According to a preferred embodiment, the implantable material is considered inhibitory if the conditioned media inhibits about 20% of what the heparin control is able to inhibit.

To evaluate inhibition of thrombosis in vitro, the level of heparan sulfate associated with the cultured endothelial cells is determined. Heparan sulfate has both anti-proliferative and anti-thrombotic properties. Using either the routine dimethylmethylene blue-chondroitinase ABC spectrophotometric assay or an ELISA assay, both assays are described in detail above, the concentration of heparan sulfate per $10^6$ cells is calculated. The implantable material can be used for the purposes described herein when the heparan sulfate in the conditioned media is at least about 0.5-1.0, preferably at least about 1.0 microg/$10^6$ cells/day.

Another method to evaluate inhibition of thrombosis involves determining the magnitude of inhibition of platelet aggregation in vitro associated with platelet rich-plasma. Porcine plasma is obtained by the addition of sodium citrate to porcine blood samples at room temperature. Citrated plasma is centrifuged at a gentle speed, to draw red and white blood cells into a pellet, leaving platelets suspended in the plasma. Conditioned media is prepared from post-confluent endothelial cell cultures and added to aliquots of the platelet-rich plasma. A platelet aggregating agent (agonist) is added to the plasma as control. Platelet agonists commonly include arachidonate, ADP, collagen, epinephrine, and ristocetin (available from Sigma-Aldrich Co., St. Louis, MO.). An additional aliquot of plasma has no platelet agonist or conditioned media added, to assess for baseline spontaneous platelet aggregation. A positive control for inhibition of platelet aggregation is also included in each assay. Exemplary positive controls include aspirin, heparin, abciximab (the product monoclonal antibody glycoprotein IIb/IIIa receptor antagonist commonly known as REOPRO, Eli Lilly, Indianapolis, Ind.), tirofiban (the product antiplatelet drug commonly known as AGGRASTAT, Merck & Co., Inc., Whitehouse Station, N.J.) or eptifibatide (the product antiplatelet drug commonly known as INTEGRILIN, Millennium Pharmaceuticals, Inc., Cambridge, Mass.). The resulting platelet aggregation of all test conditions are then measured using an aggregometer. The aggregometer measures platelet aggregation by monitoring optical density. As platelets aggregate, more light can pass through the specimen. The aggregometer reports results in "platelet aggregation units," a function of the rate at which platelets aggregate. Aggregation is assessed as maximal aggregation at 6 minutes after the addition of the agonist. The effect of conditioned media on platelet aggregation is determined by comparing baseline platelet aggregation before the addition of conditioned medium with that after exposure of platelet-rich plasma to conditioned medium, and to the positive control. Results are expressed as a percentage of the baseline. The magnitude of inhibition associated with the conditioned media samples are compared to the magnitude of inhibition associated with the positive control. According to a preferred embodiment, the implantable material is considered inhibitory if the conditioned media inhibits about 20% of what the positive control is able to inhibit.

When ready for implantation, the implantable material comprising a flexible planar form is supplied in final product containers, each preferably containing a 1×4×0.3 cm (1.2 cm$^3$) sterile piece with preferably approximately 5-8×$10^5$ preferably at least about 4×$10^5$ cells/cm$^3$ and at least about 90% viable cells, for example, human aortic endothelial cells derived from a single cadaver donor source, per cubic centimeter in approximately 45-60 ml, preferably about 50 ml, endothelial growth medium (for example, endothelial growth medium (EGM-2) containing no phenol red and no antibiotics. When porcine aortic endothelial cells are used, the growth medium is also EBM-2 containing no phenol red, but supplemented with 5% FBS and 50 µg/ml gentamicin.

In other preferred embodiments, implantable material comprising a flowable particulate form is supplied in final product containers, including, for example, sealed tissue culture containers modified with filter caps or pre-loaded syringes, each preferably containing about 50-60 mg of particulate material engrafted with about 7×$10^5$ to about 1×$10^6$ total endothelial cells in about 45-60 ml, preferably about 50 ml, endothelial growth medium per aliquot.

Shelf-Life of Implantable Material. The implantable material comprising a confluent, near-confluent or post-confluent population of cells can be maintained at room temperature in a stable and viable condition for at least two weeks. Preferably, such implantable material is maintained in about 45-60 ml, more preferably 50 ml, transport media with or without additional FBS. Transport media comprises EGM-2 media without phenol red. FBS can be added to the volume of transport media up to about 10% FBS, or a total concentration of about 12% FBS. However, because FBS must be removed from the implantable material prior to implantation, it is preferred to limit the amount of FBS used in the transport media to reduce the length of rinse required prior to implantation.

Cryopreservation of Implantable Material. The confluent implantable material comprising confluent population of cells can be cryopreserved for storage and/or transport to the clinic without diminishing its clinical potency or integrity upon eventual thaw. Preferably, the implantable material is cryopreserved in a 15 ml cryovial (the product plastic cryovial commonly know as NALGENE cryovial, Nalge Nunc Int'l, Rochester, N.Y.) in a solution of about 5 ml the product cryopreservation medium commonly known as CRYOSTOR CS10 solution (BioLife Solutions, Oswego, N.Y.) containing about 5% to 20% DMSO, about 2-8% Dextran and about 50-75% FBS. Cryovials are placed in a cold iso-propanol (or any such agent which controls the freezing rate) water bath, transferred to an about −80° C. freezer for about 4 hours, and subsequently transferred to liquid nitrogen (about −150 to −165° C.).

Cryopreserved aliquots of the implantable material are then slowly thawed at room temperature for about 15 minutes, followed by an additional approximately 15 minutes in a room temperature water bath. The material is then washed about 3 times in about 15 ml wash media. Wash media comprises EBM without phenol red and with 50 µg/ml gentamicin. The first two rinse procedures are conducted for about 5 minutes at room temperature. The final rinse procedure is conducted for about 30 minutes at 37° C. in 5% $CO_2$.

Following the thaw and rinse procedures, the cryopreserved material is allowed to rest for about 48 hours in about 10 ml of recovery solution. For porcine endothelial cells, the recovery solution is EBM-2 supplemented with 5% FBS and 50 µg/ml gentamicin at 37° C. in 5% $CO_2$. For human endothelial cells, the recovery solution is EGM-2 without antibiotics. Further post-thaw conditioning can be carried out for at least another 24 hours prior to use and/or packaging for storage or transport.

Immediately prior to implantation, the medium is decanted and implantable material is rinsed in about 250-500 ml sterile saline (USP). The medium in the final product contains a small amount of FBS to maintain cell viability during transport to a clinical site if necessary. The FBS has been tested extensively for the presence of bacteria, fungi and other viral agents according to Title 9 CFR: Animal and Animal Products. A rinsing procedure is employed just prior to implantation, which decreases the amount of FBS transferred preferably to between 0-60 ng per implant.

The total cell load per human patient will be preferably approximately $1.6\text{-}2.6 \times 10^4$ cells per kg body weight, but no less than about $2 \times 10^3$ and no more than about $2 \times 10^6$ cells per kg body weight.

As contemplated herein, the implantable material of the present invention comprises cells, preferably vascular endothelial cells, which are preferably about 90% viable at a density of preferably about $4 \times 10^5$ cells/cm$^3$ of flexible planar form, and when confluent, produce conditioned media containing heparan sulfate at at least about 0.5-1.0, preferably at least about 1.0 microg/$10^6$ cell/day, TGF-$\beta_1$ at at least about 200-300, preferably at least about 300 picog/ml/day, and b-FGF below at least about 210 picog/ml, preferably no more than about 400 picog/ml.

Delivery of Implantable Material in Flexible Planar Form

General Consideration. The implantable material can be administered to a vascular access structure in a variety of forms. According to one preferred embodiment, the implantable material is a flexible planar form cut in a shape and size which is adapted for implantation adjacent to a fistula, graft, peripheral graft, or other vascular access structure and its surrounds and which can conform to the contoured surfaces of the access structure and its associated blood vessels.

According to a preferred embodiment, a single piece of implantable material is sized for application to the vascular access structure to be treated. According to another embodiment, more than one piece of implantable material in its flexible planar form, for example, two, three, four, five, six, seven, eight or more pieces of matrix material, can be applied to a single vascular access location. Additionally, more than one location along the length of a vascular access structure can be treated with one or more pieces of the implantable material. For example, in the case of an arteriovenous graft, each of the proximal venous anastomosis, the distal venous anastomosis and the distal venous section can be treated with one or more pieces of the implantable matrix material.

According to one non-limiting embodiment, the implantable material is configured to conform to an exterior surface of a blood vessel. An exemplary non-limiting planar form is illustrated in FIG. 1. With reference to FIG. 1, the exemplary flexible planar form 20 has a length 12, a width 14 and a height 16. According to one preferred embodiment, the length 12 of the flexible planar form 20 is about 2 cm to about 6 cm, the width 14 of the flexible planar form 20 is about 0.5 cm to about 2 cm, and the height 16 of the flexible planar form 20 is about 0.1 cm to about 0.5 cm.

According to another embodiment, the flexible planar form 20 can be configured as an anatomically contoured form which conforms to an exterior surface of a blood vessel or a vascular access structure. An exemplary anatomically contoured flexible planar form 20' configured for administration to a vascular access structure is depicted in FIG. 2A and discussed in greater detail below.

As explained elsewhere herein, the contoured flexible planar form 20' of FIG. 2A can be configured in a variety of geometric forms. For example, according to one embodiment, the contoured flexible planar form 20' contains several regions that define an interior slot 60. According to additional embodiments, edges of the contoured flexible planar form 20' and/or edges of the interior slot 60 are angled or curved. According to another embodiment, height 16' of the contoured flexible planar form 20' varies across length 12' and/or width 14'. Additionally, there can be one, or more than one tab 40, bridge 50 and/or slot 60, depending upon the configuration and the intended purpose of the contoured flexible planar form 20'. With respect to the feature of a slot, a slot can be defined anywhere in, on or within the contoured flexible planar form 20'. A slot can be defined to be uniform in width or varied in width. A slot can be defined as linear, non-linear or curved.

With reference to FIGS. 2B, 2C, 2D and 2E, which depict multiple embodiments of the contoured flexible planar form 20' of the present invention containing at least one slot 60, the contoured flexible planar form 20' can define one or more than one slot in certain embodiments and can be used in accordance with the methods disclosed herein. Slot 60 defined on or within a contoured flexible planar form 20' can be aligned along any edge of the contoured flexible planar form 20' or can penetrate within the interior of the contoured form 20'. Referring now to FIG. 2E, the width 66 or overall shape of slot 60 in or within the contoured flexible planar form 20' can be defined to be uniform in width or varied in width and can be defined as linear, non-linear or curved.

With reference to FIGS. 2F and 2G, the contoured flexible planar form 20' can define a slot 60 or 60' having differing widths 66 and 66', respectively.

As depicted, the slot 60' of FIG. 2G and the width 66' are representative of an embodiment wherein the practitioner, at the time of implantation, severs the flexible planar form 20' as brought elsewhere herein, thereby converting it to the contoured flexible planar form 20' depicted in FIG. 2G.

According to one embodiment, an end to side vascular anastomotic connection, such as an arteriovenous fistula, can be treated using the implantable material of the invention. The steps of an exemplary method for delivering the implantable material in a flexible planar form to an end-to-side vascular anastomosis are illustrated in FIGS. 4A, 4B and 4C.

Figure 4A:
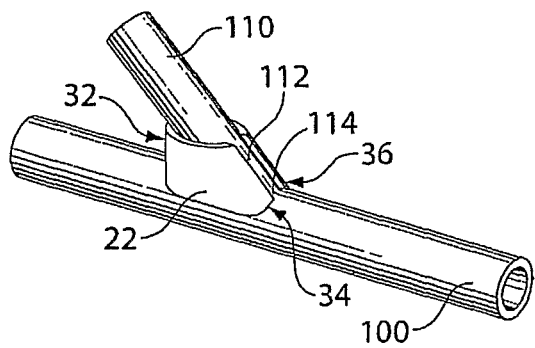
FIGS. 4A, 4B and 4C illustrate a series of steps for administering multiple flexible planar forms of implantable material to an exterior surface of a vascular anastomosis from a top perspective view according to an illustrative embodiment of the invention.

With reference to FIG. 4A, a first piece of implantable material 22 is provided to the vascular access structure by passing one end 34, or a second end 36 of the first piece of implantable material 22 under an anastomotic segment 110 until the middle 32 of the first piece of implantable material 22 is at a junction 112 where the vessels 100, 110 meet. The ends 34, 36 are then wrapped around a suture line 114 at the junction 112, keeping the implantable material centered over the suture line 114. According to one embodiment, the ends 34, 36 of the first piece of implantable matrix material 22 can overlap each other only enough to secure the first piece of implantable matrix material 22 in place. According to another embodiment, the ends 34, 36 of the first piece of implantable matrix material 22 do not overlap each other. The ends 34, 36 of the first piece of implantable matrix material 22, or of any other piece of implantable matrix material, do not have to meet each other, overlap each other, or wrap around the entire circumference of either vessel 100, 110. According to one preferred embodiment, the ends 34, 36 of the first piece of implantable material 22 wrap as far around the anastomotic junction 112 as possible without stretching or tearing. All that is required is that adequate coverage of the vessel(s) be achieved. The skilled artisan will appreciate when administration of the implantable material is correctly achieved.

Figure 4B:
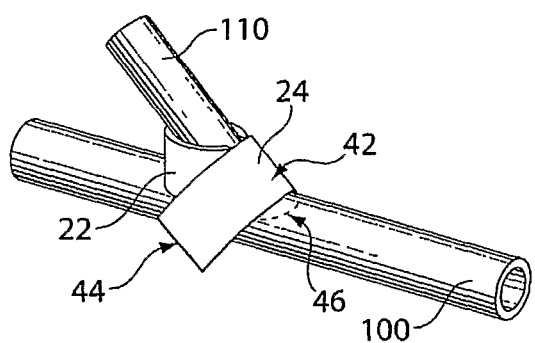

With reference to FIG. 4B, according to another embodiment, a second piece of implantable material 24 is optionally applied, with the middle 42 of the second piece of implantable material 24 centered at or adjacent or in the vicinity of the anastomotic junction 112. The ends 44, 46 of the second piece of implantable material 24 are wrapped around the vessel 100. As described with respect to the first piece of implantable material 22 in FIG. 4A, the ends 44, 46 of the second piece of implantable matrix material 24 can, but are not required to, touch, overlap, or wrap around the entire circumference of either vessel 100, 110.

Figure 4C:
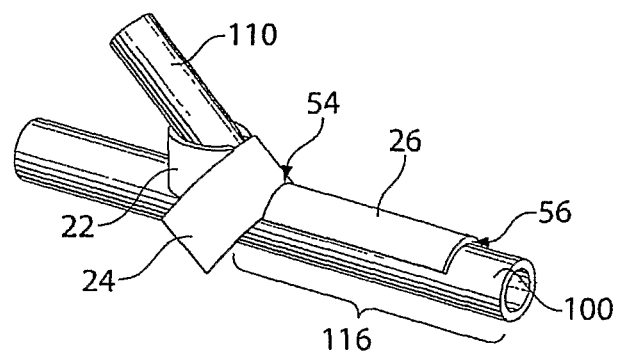

With reference to FIG. 4C, according to yet another embodiment, a third piece of implantable material 26 is optionally placed at proximal vessel segment 116 of the treated vessel 100, distal to the anastomotic junction 112. The third piece of implantable material 26, according to one embodiment, is placed longitudinally along the length of vessel 100 with a first end 54 of the third piece of implantable material 26 at, adjacent to or in the vicinity of the anastomotic junction 112 and a second end 56 of the third piece of implantable material 26 distal to the anastomotic junction 112. As described with respect to the first piece of implantable material 22 in FIG. 4A, the ends 54, 56 of the third piece of implantable matrix material 26 can, but are not required to, touch, overlap, or wrap around the entire circumference of the vessel 100.

Figure 5:
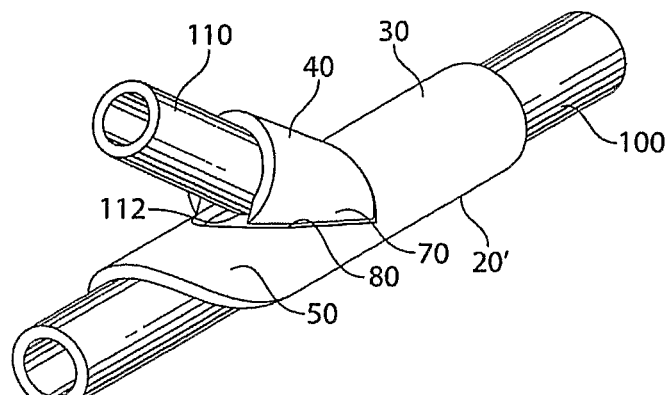
FIG. 5 is a top perspective view of a contoured form of implantable material administered to an exterior surface of a vascular anastomosis according to an illustrative embodiment of the invention.

According to an alternative embodiment, a single piece of contoured flexible planar form 20' defining a slot 60, for example the exemplary contoured form illustrated in FIG. 2A, is provided to a vascular access structure, for example, an end-to-side anastomosis. Implantation of the contoured flexible planar form 20' of the implantable material defining slot 60 at, adjacent or in the vicinity of an end-to-side anastomosis is illustrated in FIG. 5. When the implantable material is used in a wrapping fashion, it is contemplated that a single piece of implantable matrix material is adequate to treat both the anastomosis and the adjacent vasculature. Each contoured flexible planar form 20' is sized and shaped for application to a particular vascular access structure and, therefore, is preformed to provide adequate coverage and a sufficient level of endothelial cell factors and/or therapeutic agent(s) to create a homeostatic environment for that particular vascular access structure and adjacent vasculature.

With reference to FIG. 5, according to one embodiment, a single contoured 20' defining slot is provided to an anastomosis by separating the body 30 from the tab 40. The body 30 is placed along a surface of primary vessel 100. Bridge 50 is placed on a surface of primary vessel 100 and under the branch of secondary vessel 110. The tab 40 is then brought around the branched vessel 110 and the tab 40 is placed along a top surface of the branched vessel 110.

According to FIG. 5, the single piece of contoured flexible planar form 20' contains two reference points 70, 80 (see also FIG. 2A). When administered to the site of an end-to-side anastomosis, as illustrated in FIG. 5, the two reference points 70, 80 align. The first reference point 70 is located on the tab 40 and the second reference point 80 is located on the bridge 50 (see also FIG. 2A). In one embodiment of contoured flexible planar form 20', the reference points 70, 80 prior to implantation are separated by a distance of about one-half inch, preferably less than about 1 inch, more preferably about 1 inch and most preferably not more than 1.5 inch. When the contoured flexible planar form 20' is administered to the site of an anastomosis, rotation of the contoured flexible planar form 20' around the branched vessel 110 permitted by the slot feature causes the reference points 70, 80 to align.

According to one embodiment (and referencing again FIGS. 4A, 4B and 4C), for example, when treating an arteriovenous graft, the first piece of implantable material 22 and the second piece of implantable material 24 are applied to each of the proximal venous anastomosis and the distal venous anastomosis. Additionally, the third piece of implantable material 26 can be placed on the distal vein, downstream from the distal venous anastomosis.

Figure 6:
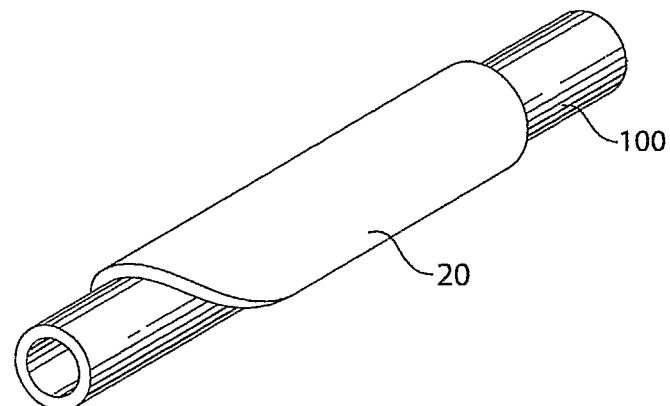
FIG. 6 is a top perspective view of a flexible planar form of implantable material administered to a tubular anatomical structure according to an illustrative embodiment of the invention.
Figure 7:
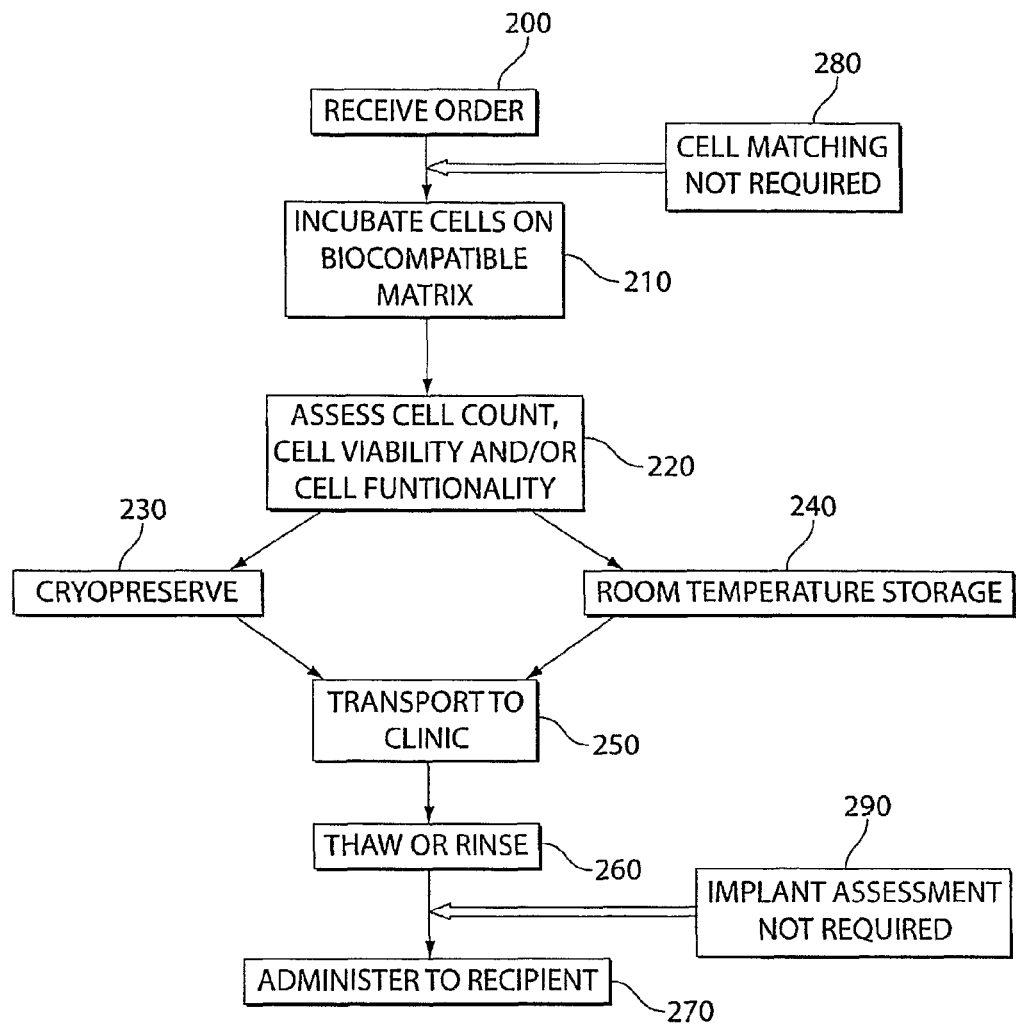
FIG. 7 is a flow chart of a method of preparing, storing and transporting an implantable material for administration to a recipient according to an illustrative embodiment of the invention.

According to yet another alternative exemplary embodiment illustrated in FIG. 6, a single piece of implantable material in flexible planar form 20 is applied to a tubular structure such as vessel 100. It is contemplated that implantable material can be applied to a tubular structure such as a vessel that does not contain a vascular access structure. For example, a venous portion downstream from a vascular access structure can experience increased inflammation, thrombosis, restenosis or occlusion resulting from vascular access structure formation or needle sticks at the vascular access structure, upstream of the treated venous portion. In such an instance, the implantable material of the present invention can treat, manage and/or ameliorate these conditions which arise at a distance from the vascular access structure.

Delivery of Implantable Material in a Flowable Composition

General Considerations. The implantable material of the present invention when in a flowable composition comprises a particulate biocompatible matrix and cells, preferably endothelial cells, more preferably vascular endothelial cells, which are about 90% viable at a preferred density of about $0.8 \times 10^4$ cells/mg, more preferred of about $1.5 \times 10^4$ cells/mg, most preferred of about $2 \times 10^4$ cells/mg, and which can produce conditioned media containing heparan sulfate at least about 0.5-1.0, preferably at least about 1.0 microg/$10^6$ cell/day, TGF-$\beta_1$ at at least about 200-300, preferably at least about 300 picog/ml/day, and b-FGF below about 200 picog/ml and preferably no more than about 400 picog/ml; and, display the earlier-described inhibitory phenotype.

For purposes of the present invention generally, administration of the flowable particulate material is localized to a site at, adjacent to or in the vicinity of the vascular access structure. The site of deposition of the implantable material is extraluminal. As contemplated herein, localized, extraluminal deposition can be accomplished as follows.

In a particularly preferred embodiment, the flowable composition is first administered percutaneously, entering the perivascular space and then deposited on an extraluminal site using a suitable needle, catheter or other suitable percutaneous injection-type delivery device. Alternatively, the flowable composition is delivered percutaneously using a needle, catheter or other suitable delivery device in conjunction with an identifying step to facilitate delivery to a desired extraluminal site. The identifying step can occur prior to or coincident with percutaneous delivery. The identifying step can be accomplished using intravascular ultrasound, other routine ultrasound, fluoroscopy, and/or endoscopy methodologies, to name but a few. The identifying step is optionally performed and not required to practice the methods of the present invention.

The flowable composition can also be administered intraluminally, i.e. endovascularly. For example, the composition can be delivered by any device able to be inserted within a blood vessel. In this instance, such an intraluminal delivery device is equipped with a traversing or penetrating device which penetrates the luminal wall of a blood vessel to reach a non-luminal surface of a blood vessel. The flowable composition is then deposited on a non-luminal surface of a blood vessel at adjacent to, or in the vicinity of the vascular access structure site.

It is contemplated herein that a non-luminal, also termed an extraluminal, surface can include an exterior or perivascular surface of a vessel, or can be within the adventitia, media, or intima of a blood vessel. For purposes of this invention, non-luminal or extraluminal is any surface except an interior surface of the lumen.

The penetrating devices contemplated herein can permit, for example, a single point of delivery or a plurality of delivery points arranged in a desired geometric configuration to accomplish delivery of flowable composition to a non-luminal surface of a blood vessel without disrupting a vascular access structure. A plurality of delivery points can be arranged, for example, in a circle, a bulls-eye, or a linear array arrangement to name but a few. The penetrating device can also be in the form of a stent perforator, such as but not limited to, a balloon stent including a plurality of delivery points.

According to a preferred embodiment of the invention, the penetrating device is inserted via the interior luminal surface of the blood vessel either proximal or distal to the site of the vascular access structure. In some clinical subjects, insertion of the penetrating device at the site of the vascular access structure could disrupt the vascular access structure and/or result in dehiscence of an arteriovenous or peripheral graft. Accordingly, in such subjects, care should be taken to insert the penetrating device at a location a distance from the vascular access structure, preferably a distance determined by the clinician governed by the specific circumstances at hand.

Preferably, flowable composition is deposited on a perivascular surface of a blood vessel, either at the site of a vascular access structure to be treated, or adjacent to or in the vicinity of the site of a vascular access structure. The composition can be deposited in a variety of locations relative to a vascular access structure, for example, at the proximal anastomosis, at the distal anastomosis, adjacent to either anastomosis, for example, upstream of the anastomosis, on the opposing exterior vessel surface from the anastomosis. According to a preferred embodiment, an adjacent site is within about 2 mm to 20 mm of the site of the vascular access structure. In another preferred embodiment, a site is within about 21 mm to 40 mm; in yet another preferred embodiment, a site is within about 41 mm to 60 mm. In another preferred embodiment, a site is within about 61 mm to 100 mm. Alternatively, an adjacent site is any other clinician-determined adjacent location where the deposited composition is capable of exhibiting a desired effect on a blood vessel in the proximity of the vascular access structure.

In another embodiment, the flowable composition is delivered directly to a surgically-exposed extraluminal site adjacent to or at or in the vicinity of the vascular access structure. In this case delivery is guided and directed by direct observation of the site. Also in this case, delivery can be aided by coincident use of an identifying step as described above. Again, the identifying step is optional.

Extraluminal Administration. For purposes of the present invention, administration of flowable composition is localized to a site adjacent to, in the vicinity of, or at a site in need of treatment. As contemplated herein, localized, extraluminal deposition can be accomplished as follows.

Flowable composition is delivered percutaneously using a needle, catheter or other suitable delivery device. Alternatively, the flowable composition is delivered percutaneously coincident with use of a guidance method to facilitate delivery to the site in need of treatment. Upon entry into the perivascular space, the clinician deposits the flowable composition on an extraluminal site at, adjacent to, or in the vicinity of the site in need of treatment. Percutaneous delivery optimally can be guided and directed by routine ultrasound, fluoroscopy, endoscopy methodologies, to name but a few.

In another embodiment, the flowable composition is delivered locally to a surgically-exposed extraluminal site adjacent to or at or in the vicinity of a site in need of treatment. In this case delivery is guided and directed by direct observation of the site in need of treatment; also in this case, delivery can be aided by coincident use of other guiding methods as described above.

Examples of flowable compositions suitable for use in this manner are disclosed in co-pending application PCT7US05/44090 filed on Dec. 6, 2005, the entire contents of which is herein incorporated by reference; and, co-pending application PCT/US05/43844 filed on Dec. 6, 2005, the entire contents of which is herein incorporated by reference.

Anastomotic Sealant. In certain other embodiments, the flowable composition of the present invention can additionally serve as an anastomotic sealant specifically or surgical sealant generally. In such a dual purpose embodiment, the composition is also effective to seal the juncture of two or more tubular structures or to seal a void in a tubular structure when contacted with an exterior surface of the structure(s), or applied in an arc on an exterior surface, or applied circumferentially. Such a sealant can eliminate a requirement for sutures which can further damage vascular tissue, for example, and contribute to luminal endothelial trauma. Such a sealant can also provide additional stability in the vicinity of an anastomosis thereby reinforcing any suture repair. All that is required is that the sealant-type properties of this dual purpose composition do not interfere with or impair coincident expression of the cells' desired phenotype and the cell-based functionality of the composition.

For purposes of certain sealant embodiments, the flowable composition comprises a biocompatible matrix which itself comprises a component having sealant properties, such as but not limited to a fibrin network, while also having the requisite properties for supporting endothelial or endothelial-like cell populations. Also, the biocompatible matrix per se can have sealant properties as well as those required to support a population of cells. In the case of other embodiments, sealant functionality can be contributed, at least in part, by the cells. For example, it is contemplated that cells associated with the composition produce a substance that can modify a substrate, such that the substrate acquires sealant properties, while also exhibiting/maintaining their requisite cellular functionality. Certain cells can produce this substance naturally while other cells can be engineered to do so.

Methods of Preparing, Storing and Transporting Implantable Material

Methods of Obtaining and Preparing Cells. The implantable material comprises allogenic, xenogeneic or autologous endothelial or endothelial-like cells. The endothelial cells are obtained from a patient, a cadaver, or a cell bank. The endothelial cells are derived from vascular tissue, more preferably from aortic tissue, most preferably coronary artery tissue, pulmonary artery tissue or iliac artery tissue. Alternatively, endothelial cells or endothelial-like cells are derived from a non-vascular tissue or organ, endothelial progenitor cells or other progenitor cells, or from stem cells. According to additional embodiments, the cells are genetically altered, modified or engineered.

Each lot of cells derived from a donor is tested extensively for endothelial cell purity, biological function, the presence of mycoplasma, bacteria, fungi, yeast, known human pathogens, and other adventitious agents. According to a preferred embodiment, cells are obtained from a donor with type O blood. The cells are further expanded to passage 2 or 4, characterized, and cryopreserved at $-140°$ C. to form a master cell bank using well-known techniques for later preparation of a working cell bank, expansion in culture, and subsequent formulation in the implantable material.

A selected master cell bank is then expanded to form a working cell bank in a T-75 flask containing about 15 mL endothelial cell growth media. The flasks are placed in an incubator maintained at approximately 37° C. and 5% $CO_2$/95% air, 90% humidity for a minimum of 30 minutes. One or two vials of cells are removed from the −160° C.-140° C. freezer and thawed at approximately 37° C. Each vial of thawed cells is seeded into two T-75 flasks at a density of about $3.0 \times 10^3$ cells per $cm^3$, preferably, but no less than $1.0 \times 10^3$ and no more than $7.0 \times 10^3$. The flasks containing the cells are returned to the incubator. After about 8-24 hours, the spent media is removed and replaced with fresh media. The media is changed every two to three days, thereafter, until the cells reach approximately 85-100% confluence preferably, but no less than 60% and no more than 100%. When the implantable material is intended for clinical application, only antibiotic-free media is used in the post-thaw culture of cells and manufacture of the implantable material of the present invention.

The endothelial growth media is then removed and the monolayer of cells is rinsed with 10 mL of HEPES buffered saline (HEPES). The HEPES is removed, and 2 mL of trypsin (about 0.25 mg/mL) is added to detach the cells from the surface of the T-75 flask. Once detachment has occurred, 3 mL of trypsin neutralizing solution (TNS) is added to stop the enzymatic reaction. An additional 5 mL of HEPES is added, and the cells are enumerated using a hemocytometer. The cell suspension is centrifuged and adjusted to a density of about $1.75 \times 10^6$ cells/mL using EGM-2 without antibiotics.

If the cells are to be frozen to form a working cell bank, the media is supplemented with an additional 10% FBS (final 12% FBS) and 10% dimethylsufoxide (DMSO). One-milliliter volumes of the resulting cell suspension are dispersed into cryovials and placed into a freezer at −80° C. for 4-24 hours. The frozen cells, i.e., the working cell bank, are then transferred to a freezer set at −140° C. for storage until use. The working cell bank is frozen at passage 5.

Methods of Preparing the Implantable Material. Precut pieces of a biocompatible matrix or an aliquot of flowable matrix are rehydrated by the addition of EGM-2 without antibiotics at approximately 37° C. and 5% $CO_2$/95% air for 12 to 48 hours. The matrix material is then removed from its rehydration container and placed in an individual tissue culture dish. The matrix material is seeded with cells from the working cell bank at a preferred density of approximately $1.5 \text{-} 2.0 \times 10^5$ cells ($1.25 \text{-} 1.66 \times 10^5$ cells/$cm^3$ of matrix) and placed in an incubator maintained at approximately 37° C. and 5% $CO_2$/95% air, 90% humidity for 3-4 hours to facilitate cell attachment. According to one embodiment, the seeded matrix is then placed into an individual sealable container or tube, fitted with a cap containing a 0.2 μm filter with EGM-2 and incubated at approximately 37° C. and 5% $CO_2$/95% air. The media is changed every two to three days, thereafter, until the cells have reached confluence. According to an alternative embodiment, the seeded matrix is placed into an individual sealable container or tube, fitted with a plug seal cap and purged with 10% $CO_2$. According to this method, the container is purged with 10% $CO_2$ at each media change.

Methods of Determining Cell Confluence and Functionality. A sample of implantable material is removed on or around days 3 or 4, 6 or 7, 9 or 10, and 12 or 13. The cells are counted and assessed for viability and a growth curve is constructed and evaluated in order to assess the growth characteristics and to determine whether confluence, near-confluence or post-confluence has been achieved. Cell counts are achieved by complete digestion of the aliquot of implantable material with a solution of 0.5 mg/mL collagenase in a HEPES/$CaCl_2$ solution. After measuring the volume of the digested implantable material, a known volume of cell suspension is diluted with 0.4% trypan blue (4:1 cells to trypan blue) and viability assessed by trypan blue exclusion. Viable, non-viable and total cells are enumerated using a hemocytometer. Growth curves are constructed by plotting the number of viable cells versus the number of days in culture. Preferably, an implantable material comprising cells is implanted after cells reach confluence but post-confluent or near-confluent cells can be used. If the cells are not confluent by day 12 or 13, the media is changed and incubation is continued for an additional day. This process is continued until confluence is achieved or until 14 days post-seeding. On day 14, if the cells are not yet confluent, the lot is typically but not necessarily discarded. If the cells are determined to be confluent after performing in-process checks, a final media change is performed. This final media change is performed using EGM-2 without phenol red and without antibiotics. Immediately following the media change, the tubes are tightly fitted with sterile plug seal caps for shipping.

The implantable material is further tested for indicia of functionality prior to implantation. For example, conditioned media are collected during the culture period to ascertain levels of heparan sulfate, transforming growth factor-$\beta_1$ (TGF-$\beta_1$), basic fibroblast growth factor (b-FGF), and nitric oxide (NO) produced by the cultured endothelial cells and the ability of the cells to inhibit smooth muscle cell growth and thrombosis in vitro. The conditioned media are evaluated according to previously described assays and parameters. A currently preferred assay is the heparan sulfate assay which can be used alone to confirm functionality. Alternatively, it can be used in combination with one or more of the assays for .TGF-$\beta_1$, b-FGF, and NO produced by the engrafted cells and/or in combination with the in vitro inhibit smooth muscle cell assay described elsewhere herein.

Compositions and Methods of Cryopreserving Implantable Material. The implantable material, comprising a population of near-confluent, confluent, or post-confluent cells engrafted in a biocompatible matrix, can be cryopreserved for extended storage over months to years, or indefinitely. In addition to reducing manufacturing time and costs, cryopreservation provides available, fully tested, viable and confirmed functional implantable material for clinical use at any time and without any production or transportation related delays.

The implantable material can be cryopreserved when the cells are near-confluent, confluent, or post-confluent. According to various embodiments, the implantable material is cryopreserved 10 to 14 days following seeding of the cells in the biocompatible matrix, more preferably 10 to 12 days following seeding, and most preferably 12 days following seeding. In general, endothelial cells are pre-confluent or confluent on or around 10 days following seeding and are 2-3 days post-confluent on or around 12 days following seeding.

Prior to and optionally following cryopreservation, the implantable material is evaluated for cell number, viability and indications of function. Exemplary cell function assays include evaluation of levels of heparan sulfate (HS), transforming growth factor (TGF)-$\beta_1$, basic fibroblast growth factor (b-FGF), and nitric oxide (NO) and ability to inhibit cultured smooth muscle cell (SMC) growth. In addition, the manufacturer and/or the physician can assess cell viability using a trypan blue assay, described in detail above, prior to administration of the implantable material to a patient. According to a preferred embodiment, the implantable material is acceptable if the total cell count is equal to or greater than 400,000 cells/$cm^3$, 80% to 90% or more of the cells are viable, heparan sulfate is present at 0.23 μg/mL/day or greater, and TGF-$\beta_1$ is present at 300 pg/mL/day or greater.

According to an additional embodiment, the implantable material is acceptable if the level of b-FGF is 300 pg/mL/day or lower.

According to one embodiment, the implantable material is cryopreserved in a cryopreservation media composition comprising a cryopreservative supplemented with a polysaccharide and serum. According to a preferred embodiment, the implantable material is cryopreserved in a cryopreservation media composition comprising about 5 mL of the product cryopreservation medium commonly known as CRYOSTOR CS10 solution (BioLife Solutions, Oswego, N.Y). containing about 10% DMSO and supplemented with about 4.5% Dextran and about 50% FBS. According to additional embodiments, the concentration of FBS is greater than the amount of FBS used in cell culture, is about 20% to 80%, more preferably about 40% to 60%, and most preferably about 50%. According to additional embodiments, the concentration of DMSO is about 5% to 20% DMSO, more preferably about 7% to 15%, most preferably about 10% DMSO. According to additional embodiments, the concentration of Dextran is about 2% to 8%, more preferably about 4% to 6%, and most preferably about 4.5%. According to one embodiment, the Dextran has a molecular weight of about 10,000 to 500,000, more preferably about 20,000 to 200,000, most preferably about 70,000. According to a preferred embodiment, the cryopreservation media composition has a pH about 6.8 to 8.0, more preferably about 7.2 to 7.6, most preferably about 7.4.

According to one method of cryopreservation, the implantable material is transferred from its cell culture vial to a 15 mL cryovial (Nalgene®, Nalge Nunc Int'l, Rochester, N.Y.), to which about 5 mL of cryopreservation media composition is added. According to additional embodiments, the cryovial has a volume of about 6 to 10 mL, more preferably about 10 to 15 mL, and most preferably about 15 mL. According to one embodiment, the ratio of volume of cryopreservation media to volume of air in the cryovial is about 1:1 to 1:2, more preferably about 1:1 to 2:3, most preferably about 1:1.

According to one method of cryopreservation, the cryovial containing the implantable material and cryopreservation media composition is placed in a freezing container (the product freezing container commonly known as MR. FROSTY, Nalge Nunc Int'l, Rochester, N.Y.). Isopropanol is added to the freezing container to fill about one-half of the volume of the freezing container. According to one embodiment, the freezing container is then transferred to –20° C. freezer. According to another embodiment, the freezing container is then tranferred to a –80° C. freezer. According to a further embodiment, following about 16 hours in the –80° C. freezer, the freezing container is transferred to liquid nitrogen vapor phase (approximately –140° C. to –160° C.). According to various embodiments, the freezing container is maintained at a temperature of about –4° C. to –160° C., more preferably about -20° C., about -80° C. or -160° C., and most preferably about –140° C. to –160° C. The implantable material can remain in a cryopreserved state for 2 months, 4 months, 6 months, 8 months, 10 months, 12 months and more according to various embodiments.

If the implantable material is not thawed slowly, the biocompatible material tends to break apart in several pieces, reducing matrix integrity, cell confluency and viability. The integrity of the material is improved by thawing the implantable material slowly. According to a preferred method of slowly thawing the implantable material, the cryovial containing the frozen implantable material and cryopreservation media is removed from the freezer (about –4° C. to –80° C.) or liquid nitrogen vapor phase (approximately –40° C. to –160° C.) and thawed at room temperature for about 15 minutes followed by an additional 15 minute thaw in a room temperature water bath. The implantable material is then removed from the cryovial and washed to remove remaining cryopreservation media.

According to one embodiment, the implantable material is thawed in the laboratory for in vitro assessment. According to this embodiment, the implantable material is washed twice in 15 mL wash media (EBM-PRF and 50 µg/mL gentamicin) for 5 minutes at room temperature, followed by a final wash in about 15 mL wash media for 30 minutes at 37° C. and 5% $CO_2$. Following the wash procedures, the implantable material is placed in 10 mL EGM-2 at 37° C. and 5% $CO_2$ for a recovery period of about 48 hours. The implantable material can optionally be conditioned for an additional 24 hours prior to clinical use or for subsequent packaging of the implantable material for transport.

According to another embodiment, the implantable material is thawed in the clinic for patient implantation. According to this embodiment, the implantable material is removed from the cryovial and washed twice in about 500 mL wash media. According to various embodiments, the wash media comprises USP grade saline, Lactated Ringer's solution, and EBM-PRF at room temperature. The implantable material remains in the first wash media solution for about 1 to 40 minutes, more preferably about 2 to 25 minutes, and in the second wash media solution for about 1 to 20 minutes, more preferably about 1 to 10 minutes. The implantable material is removed from the second wash media and implanted in the patient.

Compositions and Methods of Extending the Shelf-Life of Implantable Material. Embodiments of the implantable material comprising a near-confluent, confluent, or post-confluent population of endothelial cells embedded in a biocompatible matrix can be maintained for storage and/or transport in a viable, shelf-stable condition at room temperature for about 21 to 28 days. According to additional embodiments, the implantable material can be maintained at room temperature for at least about 1 week, at least about 2 weeks, at least about 3 weeks, or at least about 4 weeks.

The implantable material can be prepared for storage at room temperature, according to various embodiments, 10 to 14 days following seeding of the cells in the biocompatible material. According to a currently preferred embodiment, the implantable material is prepared for storage at room temperature 12 days following seeding. According to another currently preferred embodiment, the implantable material is prepared for storage at room temperature 10 days following seeding.

Prior to and optionally following storage in transport media, the implantable material can be evaluated for cell number and indications of viability and function. Exemplary cell function assays include evaluation of levels of heparan sulfate (HS), transforming growth factor (TGF)-$\beta_1$, basic fibroblast growth factor (b-FGF), and nitric oxide (NO) and ability to inhibit cultured smooth muscle cell (SMC) growth. In addition, the manufacturer and/or the physician can assess cell viability using a trypan blue assay, described in detail above, prior to administration of the implantable material to a patient. According to a preferred embodiment, the implantable material is acceptable if the total cell count is equal to or greater than 400,000 cells/cm3, 80% to 90% or more of the cells are viable, heparan sulfate is present at 0.23 µg/mL/day or greater, and TGF-$\beta_1$ is present at 300 pg/mL/day or greater. According to an additional embodiment, the implantable material is acceptable if the level of b-FGF is 300 pg/mL/day or lower.

The implantable material is stored at room temperature in a transport media composition comprising supplemented EGM-2. Normal, unsupplemented EGM-2 when used for cell culture purposes contains about 2% FBS, about 0.2 mg/mL hydrocortisone, about 2 ng/mL VEGF, about 4 ng/mL hFGF, about 5 ng/mL R3-IGF-1, about 75 mg/mL ascorbic acid, about 10 ng/mL hEGF, and about 1 ng/mL heparin. According to additional embodiments, the unsupplemented EGM-2 further contains an antibiotic, including but not limited to about 30 μg/mL gentamicin or about 15 ng/mL amphotericin-B.

According to a preferred embodiment, the implantable material is stored at room temperature in a transport media composition comprising about 50 mL EGM-2 without phenol red (Cambrex BioScience, East Rutherford, N.J.) supplemented with an additional about 2 ng/mL VEGF, bringing the total concentration of VEGF in transport media to about 4 ng/mL. According to additional embodiments, normal EGM-2 is supplemented with about 0.1 to 4 ng/mL VEGF, more preferably about 1 to 3 ng/mL VEGF, and most preferably about 2 ng/mL VEGF. According to a preferred embodiment, the transport media pH prior to cell exposure is about 7.4 to 8.0. The pH of the transport media decreases as exposure to the cells increases, resulting in a transport media pH following cell exposure of about 6.8 to 7.4.

According to another embodiment, the implantable material is stored at room temperature in a transport media composition comprising about 50 mL EGM-2 without phenol red (Cambrex BioScience, East Rutherford, N.J.) supplemented with an additional about 8% FBS, bringing the total concentration of FBS in transport media to about 10%. According to additional embodiments, normal EGM-2 is supplemented with about 1 to 50% FBS, more preferably about 2 to 20% FBS, and most preferably about 8% FBS.

The volume of transport media is an important condition to maintain the viability of the implantable material for up to about 21 to 28 days at a temperature below about 37 C, for example at room temperature. The volume of transport media should be a volume sufficient to provide an optimal concentration or dilution of the cells' waste products while simultaneously providing an optimal concentration of the cells secreted beneficial products. In general, the optimal volume of transport media to maintain the implantable material increases as the temperature falls below 37° C., the cells' standard cell culture temperature. According to a preferred embodiment, the implantable material is stored at room temperature in about 50 mL of transport media. According to additional embodiments, the implantable material is stored in about 28 to 150 mL transport media, more preferably about 50 to 100 mL transport media, and most preferably about 50 mL transport media. According to one embodiment, the transport vial contains about $4.2\text{-}17 \times 10^5$ cells/cm$^3$ matrix material. According to another embodiment, the transport vial contains about $0.1\text{-}0.4 \times 10^5$ cells/mL transport media.

According to one method of shelf-life storage, the implantable material remains in its cell culture vial for storage and/or transport. According to a preferred embodiment, the cell culture vial is a 50 mL cell culture vial (Evergreen Scientific, Los Angeles, Calif.; Becton, Dickenson and Company, Franklin Lakes, N.J.). According to another method of storage, the implantable material is cultured in a 30 mL cell culture vial and then transferred from its cell culture vial to a 50 mL transport vial prior to storage and/or transport to accommodate a larger volume of transport media. According to a further method of storage, the implantable material is transferred from its cell culture vial to a 150 mL transport vial (Nalgene', Nalge Nunc Int'l, Rochester, N.Y.). According to various embodiments, the transport vial has a volume of about 53 to 58 mL, more preferably about 54 to 56 mL, and most preferably about 57 mL. According to a preferred embodiment, the transport vial contains at least about 5 to 6 mL of 5% $CO_2$/95% air, or a ratio of volume of air to volume of media and implantable material of about 1:8 to 1:12, more preferably about 1:10. The filter cap is removed from the vial and the vial is sealed with a plug seal cap (Evergreen Scientific, Los Angeles, Calif.) and the caps tightened prior to storage at room temperature.

Packaging for Ground and Air Transport of Implantable Material. Transport vials of the implantable material packaged for storage at ambient temperature and intended for transport via ground carrier or air carrier are packaged according to one of the following methods. According to one method, three transport vials are placed into each of two re-sealable plastic bags and the bags sealed. Two bags (six vials) are then packaged into an inner box. According to another method, each vial is placed into an individual re-sealable plastic bag and the bag sealed. Four vials are then packaged into a plastic cylinder. Each of the described packaging configurations is designed to provide multiple boundary layers to protect the product from thermal effects, transit damage and to maintain a clean, sterile environment. The inner box or plastic cylinder is then packed into an insulated outer-shipping box. The outer-shipping box utilizes foam inserts and gel packs to maintain the desired thermal environment (preferably about 15-25° C.) and to protect against transit damage. Included with every lot is the appropriate documentation. The vials containing the implantable material as well as the inner box or plastic cylinder and the outer shipping box will also be appropriately labeled.

Cryovials of the implantable material packaged for storage at −20° C., −80° C., or −140° C. to −160° C. and intended for transport via ground carrier or air carrier are packaged according to one of the following methods. According to one method, each cryovial is placed into an individual re-sealable plastic bag and the bag sealed. The cryovials are then packaged into an insulated inner box, for example, the product closed-cell extruded polystyrene foam commonly known as STYROFOAM (Dow Chemical Co., Midland, Mich.) inner box, containing dry ice. The cryovials are buried or submerging in the dry ice. The inner box utilizes dry ice (preferably about −80° C.) to maintain the desired thermal environment (preferably about −80° C. to −160° C.) and to protect the cryovials against transit damage. The product closed-cell extruded polystyrene foam commonly known as STYROFOAM inner box is then packed into an insulated outer-shipping box. According to one embodiment, upon arrival at the clinic, the cryovials are placed into a −20° C. or −80° C. freezer for an extended storage period. According to another embodiment, upon arrival at the clinic, the cryovials are subjected to the rinse and thaw procedure, described above, for immediate patient implantation.

According to various embodiments, the implantable material can be maintained by cryopreservation in cryopreservation media for about a month to a year, preceded and/or followed by about at least three weeks of storage in transport media at about room temperature prior to use while maintaining the viability and functionality of the implantable material.

Immediately prior to implantation, the implantable material is removed from the transport, cryopreservation or conditioning media and rinsed two or three times in about 250-500 mL sterile saline (USP) to remove remaining media constituents, including FBS. A sample aliquot of the implantable material can be tested for viability by the manufacturer and/or by the physician prior to implantation, for example, using a trypan blue assay, described in detail above.

Upon receipt by applicant or applicant's agent of a request for implantable materials, a series of events exemplified as follows will be initiated: A cryopreserved implant will be prepared for transport in dry ice as described above, an implant will be prepared for transport at room temperature as described above, or an implant will be prepared by seeding a biocompatible matrix with cells and permitted to grow in vitro until it exhibits one or more of the functional phenotypes described above. Cells for seeding can be obtained from a cell bank as explained above, or can be obtained directly from the intended recipient of the implant. Regardless of the source or type of cell present in an implantable material, it is not required that the cell is first tested for compatibility with the intended recipient. That is, treatment with an implantable material of the present invention does not require a cell typing, cell matching or cell compatibility test relative to the intended recipient prior to manufacture or implantation. When prepared in accordance with the teachings set forth herein, treatment with an implantable material is a cell typing-independent, cell compatibility-free, match-free treatment regimen. This feature of the present invention stands in sharp contrast to conventional cell-, tissue- or organ based treatments which routinely require pre-testing to determine that a match exists between the intended recipient and the cell, tissue or organ to be implanted; in the absence of a match, no treatment will occur. The present invention obviates the need for a pre-test to determine whether a match exists thereby providing the clinician with a readily available, uninterrupted supply of implantable materials for treatment of any one of the injuries or diseases described herein.

EXAMPLES

Example 1

Human AV Fistula Study

This example provides experimental protocols for testing and using a preferred embodiment of implantable material comprising vascular endothelial cells to enhance maturation of a fistula and/or prevent failure of a fistula to mature. Using standard surgical procedures, an arteriovenous fistula is created at the desired anatomic location. The implantable material in a flexible planar form is then disposed in the perivascular space adjacent to the surgically created fistula; the details of one exemplary procedure are set forth below. As described earlier, the placement and configuration of the implantable material can be varied to suit the clinical circumstances. In this study, a preferred exemplary flexible planar form is depicted in at least FIG. 1 or 2A.

The experiments and protocols set forth below provide sufficient guidance:

1. To evaluate arteriovenous fistula failure to mature at 3 months.

For this study, failure to mature is defined as the inability to permit repetitive cannulation of the fistula for dialysis and to obtain sufficient dialysis blood flow within the range of 35-500 mL/min, with a preferred blood flow of at least 350 mL/min, within about 12 weeks after fistula creation. Standard clinical practices will be employed.

2. To evaluate access flow rate and anatomy (% area stenosis) by color flow Doppler ultrasound at day 5, 2 weeks, 1, 3 and 6 months and at subsequent time points.

Decrement in absolute access flow between the baseline measurement (day 5 post-surgical) and 6 months post-surgical as measured by color flow Doppler ultrasound. Magnitude of stenosis determined by Doppler ultrasound at 6 months when compared to baseline (day 5 post-surgical value). Standard clinical practices will be employed.

3. To evaluate the HLA antibody response associated with the use of an allogeneic cell product.

Quantitative immunological assessment of the presence of donor HLA antibodies at 5 days, 2 weeks, 1, 3 and 6 months post-surgery compared to pre-surgical levels. Standard clinical practices will be employed.

Specifically, the study includes 10 human uremic patients undergoing arteriovenous fistula surgery. Those patients who have undergone AV fistula surgery will receive (immediately after surgery) application of two (2) 1×4×0.3 cm (1.2 cm$^3$) embodiments of a flexible planar form; one (i) placed at the anastomotic juncture and the other is placed longitudinally on the proximal vein segment, distal to the anastomosis. An additional 5 patients will be enrolled but will not receive implants. These 5 patients will be used for comparison to standard of care.

Clinical follow-ups will be performed at 5 days, 2 weeks and at 1, 3 and 6 months. Access flow measurements using color-flow Doppler ultrasound will be performed at day 5 to establish a baseline level, followed at 2 weeks, 1 month, 3 months and 6 months post-surgery. Patients that exhibit an absolute flow of less than about 350 mL/min, or exhibit greater than 25% reduction in flow from the previous measurement, or exhibit greater than 50% area stenosis (as measured by Doppler ultrasound) will be referred for angiography. Remedial clinical intervention such as angioplasty will be permitted for stenotic lesions of greater than 50% as determined by angiography. Patients with fistula that fail to mature within 12 weeks will be referred for diagnostic imaging. Standard remedial clinical intervention, including angioplasty and surgery to tie off side branches or to revise the fistula, will be permitted to assist with functional maturation in fistulae that have failed to mature within 12 weeks. The duration of study participation for each patient will be 6 months.

Accordingly, a total of 15 patients will be enrolled in this trial. Ten patients will each receive 2 implants, and 5 patients receiving standard of care will be used for comparison. Patients undergoing AV fistula placement for hemodialysis access will also be enrolled.

The ten treated patients treated with the implantable material of this invention will each have standard AV fistula placement, medications, treatments, and implants, according to the following study design. The first 5 of these patients will receive two implants in a flexible planar form, one at the anastomotic site and one placed longitudinally on the proximal vein segment, distal to the anastomosis. Following treatment of the last patient within this first group, a one-month observation period will occur prior to treatment of the next group. Following a satisfactory review of the 1-month data from the first 5 patients, the final 5 patients will be treated.

Five patients will be enrolled in the clinical trial and will receive standard AV fistula placement, medications, treatments but no implantable material. These patients will be used for comparison to standard of care and will receive similar imaging and immunological follow-up as implant-treated patients.

Conventional AV fistula surgery procedures are to be performed according to standard operative techniques. Upon completion of the fistula, but prior to implantation, measurement of the outflow vein diameter will be made.

Non-toothed forceps will be used to gently lift the implantable material in planar form from the rinse bowls. The implantable material will be applied after the access surgery is completed and flow through the fistula is established with all baseline measurements having been made. All bleeding will be controlled and the area to be treated made as dry as possible before placement of the implantable material. The area(s) will not be irrigated after implant placement. One or two implant(s) will be used to treat the anastomotic site. The other implant will be used to treat the proximal vein segment, distal to the anastomosis. In certain embodiments, the end to side vascular connections will be treated by passing an end of the implant under the anastomotic segment until the middle of the implant is at the point where the vessels meet. Both ends are then wrapped around the suture line keeping the implant centered over the suture line. The proximal venous segment (distal to the venous-arterial anastomosis) will be treated by placing the implantable material longitudinally along the length of vein starting at the anastomotic site. The implantable material does not need to completely wrap around the circumference of the vein.

Patients will be followed with standard nursing procedures during the course of hospital recovery following AV fistula surgery. Vital signs will be closely monitored. Concomitant medications will be recorded. Patients will be instructed on requirements for follow-up visits at 5 days, 2 weeks, and at 1, 3, and 6 months.

Access flow will be recorded at day 5 (baseline), 2 weeks and thereafter at 1, 3 and 6 months post-surgery. The degree of stenosis will also be determined by Doppler ultrasound at day 5 to establish a baseline level and again at 2 weeks, 1, 3 and 6 months for comparison purposes. A 5-cc whole blood specimen will be obtained to provide serum for determination of anti-HLA antibody levels at 5 days, 2 weeks, 1, 3 and 6 months post-surgery.

Access flow will be determined using color-flow Doppler ultrasound at day 5 (±24 hr) to establish a baseline measurement and at 2 weeks (±2 days), 1 month (±4 days), 3, and 6 months (±7 days) post-surgery. Patients that exhibit an absolute flow of less than about 350 mL/min, or exhibit greater than 25% reduction in flow from their previous measurement or exhibit greater than 50% area stenosis (as measured Doppler ultrasound) will be referred for angiography. Remedial clinical intervention such as angioplasty will be permitted for stenotic lesions of greater than 50% stenosis as determined by angiography. Patients with fistula that fail to mature within 12 weeks will be referred for diagnostic imaging. Standard remedial clinical intervention, including angioplasty and surgery to tie off side branches or to revise the fistula, will be permitted to assist with functional maturation in fistulae that have failed to mature within 12 weeks. Such intervention can be followed by implantation of the implantable material to enhance maturation of the revised fistula and/or maintain functionality of the revised fistula and rescue a failing or failed fistula.

Expected Results of AV Fistula Study. It is expected that patients treated with the implantable material of the present invention as described above will display one or more indicia of an enhancement of fistula maturation and/or of prevention of fistula failure to mature. Specifically, the treated patients individually will display, for example, an improved blood flow, up to a flow sufficient for dialysis (e.g., a blood flow within the range of 35-500 mL/min and preferably at least 350 ml/min) and/or an improved ability to repeatedly cannulate the fistula for dialysis. Another of the indicia of fistula maturation is vein wall thickness; a successfully mature or maturing fistula exhibits vein wall thickening. This will be measured using intravascular ultrasound (IVUS) according to standard clinical practices. Briefly, IVUS will be used to measure vein wall thickness and delineate between intimal and medial thickness. The treated or control fistula will be cannulated and the ultrasound probe placed inside the target veins and arteries. Yet another indicia of a functioning fistula is adequate lumen diameter. It is expected that the implantable material of the present invention will permit maintenance of adequate lumen diameter thereby permitting unimpeded blood flow at rates suitable for effective dialysis, i.e., blood flow that is marginally greater than the pump rate of the dialysis machine; or, at least a blood rate adequate to prevent recirculation during dialysis. Lumen diameter will be monitored serially using angiography of the fistula beginning on day 5 after fistula creation and thereafter at least 3 months post surgery. Narrowing of the lumen post-surgery will be correlated with blood flow rates using standard Doppler ultrasound protocols. It is expected that the implantable material will prevent or delay narrowing that impedes blood flow below a rate suitable for dialysis as described herein. This narrowing of the lumen which characterizes a failed fistula can arise due to stenosis and associated thickening of the intima, or it can arise by a shrinkage and/or contraction of the vessel without any associated thickening. In the case of actual thickening, an angioplasty intervention is currently a standard clinical means; in the case of shrinkage and/or contraction due, for example, to negative tissue remodeling, dilatation is currently a standard clinical intervention. It is expected that an implant-treated fistula will not require angioplasty or dilatation.

As a group, the treated patients are expected to show at least incremental differences in at least one of these aforementioned indicia of maturation as compared to controls.

Example 2

AV Graft Animal Study

This example provides experimental protocols for testing and using a preferred embodiment of the present invention to promote formation of a functional AV graft in animal test subjects. Using standard surgical procedures, an AV graft was created between the carotid artery and the jugular vein. Implantable material was then disposed in the perivascular space adjacent to each surgically created AV graft anastomosis; the details of one exemplary procedure are set forth below. As described earlier, the placement and configuration of implantable material can be varied. In this study, the implantable material was in a flexible planar form as depicted in FIGS. 4A, 4B and 4C.

Specifically, the study included 26 porcine test subjects undergoing AV graft surgery. Conventional AV graft surgery procedures were performed according to standard operative techniques. Implantable material was applied to the AV graft anastomoses and surrounds as described below after the graft surgery was completed and flow through the graft was established.

For each test subject undergoing AV graft surgery, one six-millimeter internal diameter PTFE graft was placed between the left common carotid artery and right external jugular vein of the test subject. An oblique end-to-side anastomosis was created at each end of the graft using a running 6-0 prolene suture. All test subjects received intra-operative heparin and administered daily aspirin following surgery.

Ten of the test subjects received implantable material comprising aortic endothelial cells on the day of surgery. Five such implants were applied to each test subject. Two implants were wrapped around each of the two anastomotic sites. In this circumstance, one end of the implantable material was passed under the anastomotic segment until the middle of the implant was at the point where the vessel and graft meet. Both ends were then wrapped around the suture line keeping the implant centered over the suture line. The ends overlapped minimally to secure the material in place. An additional single implant was placed longitudinally along the length of the proximal venous segment starting at the anastomosis, of each test subject. The implant did not completely wrap around the circumference of the vein.

The anastomotic sites were wrapped with implantable material, for example, as illustrated in the FIGS. 4A and 4B. Additionally, the proximal venous segment (distal to the venous-arterial anastomosis) was treated by placing the implantable material longitudinally along the length of vein starting at the anastomotic site, for example, as illustrated in FIG. 4C.

Ten test subjects received control implants without cells, wrapped around the anastomotic sites and placed on the proximal venous segment of the graft on the day of surgery, for example, as depicted in FIGS. 4A, 4B and 4C. An additional 6 test subjects did not receive either type of implant. These 6 test subjects were used for comparison to standard of care. The total cell load based on body weight was approximately $2.5 \times 10^5$ cells per kg. It is expected that this cell load is approximately at least 6-10 times the estimated cell load which will be used in a human clinical study as described below.

Surgical Procedure. A 15-cm midline longitudinal neck incision was made and the left common carotid artery isolated followed by the right external jugular vein. An 8 cm segment of vein was freed from surrounding tissues and all tributaries off the vein were ligated with 3-0 silk sutures. The left carotid artery was clamped and a 7-mm diameter circumferential arteriotomy performed. An oblique end-to-side anastomosis was made between the artery and a 6-mm internal diameter PTFE graft using a running 6-0 prolene suture. Once fashioned, the arterial clamp was removed and the graft flushed with heparin-saline solution. Flow was documented through the artery into the graft. The graft was then tunneled beneath the sternocleidomastoid muscles and brought into the proximity of the right external jugular vein.

A 7-mm diameter circumferential venotomy was performed directly in the external jugular vein. The arteriovenous graft was then completed with an oblique end-to-side anastomosis between the PTFE graft and the right external jugular vein using a running 6-0 prolene suture (the length of graft was between 15-25 cm and recorded at the time of placement). All clamps were removed and flow through the graft was confirmed. The left carotid artery distal to the PTFE anastomosis was doubly tied off with 3-0 silk sutures.

Following completion of the anastomoses, the PTFE arteriovenous graft was positioned to prevent kinking. The PTFE arteriovenous graft was percutaneously cannulated with a 23-gauge butterfly needle just distal to the carotid artery-graft anastomosis. To confirm placement, blood was aspirated into the system with a 10 cc syringe. The system was then flushed with 10 cc's of saline. A C-arm fluoroscope was then placed over the neck of the study animal so that the venous-graft anastomosis and the venous outflow tract could be visualized. Under continuous fluoroscopy, 10-15 cc's of iodinated contrast (Renograffin, full strength) was injected. The cine angiography was recorded and stored for comparison to the pre-sacrifice angiogram.

After completion of the angiography, the anastomotic sites were wrapped in a wet 4"×4" gauze sponge. Pressure was maintained on the anastomotic sites for a period of approximately 5 minutes, before removing the gauze sponges and inspecting the anastomotic sites. If hemostasis had not yet been achieved, as was evidenced by oozing of blood, the site was again wrapped for another 5 minutes. Additional sutures were placed at the discretion of the surgeon if the hemorrhage from the site was severe. Once hemostasis had been achieved, the neck wound was filled with sterile saline and flow probe analysis performed at the distal venous outflow tract using a 6-mm Transonic flow probe. The saline was removed, if necessary, and the anastomoses made as dry as possible and treated with either implantable material comprising aortic endothelial cells or control implants. Sites were not treated with either type of implant until all bleeding had been controlled, flow through the graft confirmed and the area made as dry as possible. When complete, the wound was closed in layers and the animal was allowed to recover from anesthesia.

Heparin was administered prior to surgery as a 100 U/kg bolus injection plus a 35 U/kg/hr continuous infusion and maintained until the end of surgery. Additional bolus doses (100 U/kg) were administered, as necessary to maintain ACTs≥200 seconds.

Graft Patency. AV graft patency was confirmed by access flow measurements using color-flow Doppler ultrasound and Transonic flow probe (Transonic Systems, Inc., Ithaca, N.Y.) immediately after surgery, 3-7 days post surgery and once per week thereafter. Grafts were monitored closely for blood flow.

Pathology Procedures. Animal test subjects were anesthetized using sodium pentobarbital (65 mg/kg, IV). The PTFE grafts were exposed and digital photography of the PTFE graft and the venous anastomosis performed. The PTFE arteriovenous graft was then percutaneously cannulated with a 23-gauge butterfly needle just distal to the carotid artery-graft anastomosis. To confirm placement, blood was aspirated into the system with a 10 cc syringe. The system was then flushed with 10 cc's of saline. A C-arm fluoroscope was then placed over the neck of the animal so that the venous-graft anastomosis and the venous outflow tract could be visualized. Under continuous fluoroscopy, 10-15 cc's of iodinated contrast (Renograffin, full strength) was injected. The cine angiography was recorded at 0° and 90° angles to the PTFE graft. Graft patency and degree of stenosis of the venous outflow tract was determined by blinded read of the necropsy angiograms in paired comparison with post-placement angiograms. Angiograms were graded on a scale of 0-5 depending upon the degree of stenosis observed in the angiogram. The grading scheme employed was as follows: 0=0% stenosis, 1=20% stenosis, 2=40% stenosis, 3=60% stenosis, 4=80% stenosis and 5=100% stenosis. It was anticipated that the grafts treated with the implantable material of the present invention would exhibit a decreased percent stenosis compared to control upon examination of the angiograms.

Histology. Half of the animal test subjects (5 cell engrafted implant subjects; 5 control implant subjects; 3 subjects without implants) were euthanized 3 days following surgery. The remaining animal test subjects (5 cell engrafted implant subjects; 5 control implant subjects; 3 subjects without implants) were euthanized one month following surgery.

A limited necropsy, defined as the macroscopic examination of the administration site, including all anastomotic and proximal venous sites, and surrounding tissue including draining lymph nodes was performed on all test subjects. Tissue from major organs, including brain, lungs, kidneys, liver, heart and spleen, were collected and saved for all test subjects euthanized at one month following surgery. The organs were to be analyzed only if unusual findings arose from macroscopic examination of the external surface of the body or from the microscopic examination of administration sites and surrounding tissue. No unusual findings arose that warranted further examination of the major organs in any of the animals enrolled into the study.

All AV graft anastomotic sites and surrounding tissues, including 5-cm segments each of the anastomosed vein and artery, were trimmed, fixed in 10% formalin (or equivalent) and embedded in glycolmethacrylate (or equivalent). Using approximately 3 μm-thick sections cut with a C-profile stainless steel knife (or equivalent), sections were prepared from at least three regions: the vein graft anastomosis, the graft-artery anastomosis, and the venous outflow tract. Three sections were made transversely through the vein graft anastomosis. Five sections were made through the venous outflow tract (therefore covering 1.5-cm of outflow vein). Three sections were made through the graft-artery anastomosis at 1-mm intervals. These sections were mounted on gelatin-coated (or equivalent) glass slides and stained with hematoxylin and eosin or Verhoeff's elastin stain.

Perivascular and luminal inflammation will be determined both acutely (3 day subjects) and chronically (1 month subjects). Acute inflammation is marked by granulocytes, primarily neutrophils, while chronic inflammation is marked by macrophages and lymphocytes. Additionally, sections may also be stained with the following specific markers: anti-CD45 to identify leukocytes, anti-CD3 to identify T cells, CD79a to identify B cells and MAC387 to identify monocytes/macrophages.

The stained slides will be examined and scored for the presence of smooth muscle cells and endothelial cells and for indications of integration between the arterial or venous anastomosis and the artificial graft material. All sections of the isolated tissue, including the graft material, the intima/pseudointima, the inner portion of the media near the lumen, the outer portion of the media near the adventitia, and the adventitia for each of the vein graft anastomosis, the graft-artery anastomosis, and the venous outflow tract will be evaluated and scored. The size of each of the tissue compartments, for example, the intima, the media and the adventitia, will be measured in microns. Each section will be evaluated for the presence and/or extent of each of the following criteria. Indicia of inflammation will be evaluated, including but not limited to, the presence and extent of neutrophils, lymphocytes, macrophages, eosinophils, giant cells and plasma cells. Graft sections will be evaluated for the presence of fibroblasts, neovascularization, calcification, hemorrhage, congestion, fibrin, graft fibrosis and graft infiltration. Tissue sections additionally will be evaluated for indicia of degeneration, including but not limited to the degeneration, elastin loss and/or the absence of the tissue portion, smooth muscle myofiber vacuolation and/or calcification of the tissue. Tissue sections also will be evaluated for endothelial cell proliferation, subintimal cell proliferation, including but not limited to neovascularization and the presence of smooth muscle myofiber, fibroblasts and fibrosis. Each of the measured tissue sections also will be evaluated for tissue necrosis and the presence of foreign material. Scores will be assigned for each variable on a scale of 0 through 4 (0=no significant changes; 1=minimal; 2=mild; 3=moderate; and 4=severe).

Additional sections of arteriovenous graft anastomotic sites from the 1-month animal test subjects only, will be mounted on glass slides and stained (Verhoeff's elastin) for morphometric analysis. Measurements of the luminal, medial, intimal and total vessel volume will be taken using computerized digital planimetry with a video microscope and customized software for each section. The extent of intimal hyperplasia will be determined for each section. One method of quantifying intimal hyperplasia is by normalizing the intima area by the total vessel wall area [(intima, mm$^2$)/(intima+media, mm$^2$)], or by determining the residual lumen [(lumen, mm$^2$)/(lumen+intima, mm$^2$)].

Results for AV Graft Animal Subjects. Subjects treated with the implantable material of the present invention as described above displayed one or more indicia of formation of a clinically functional AV graft. AV grafts treated in accordance with the materials and methods disclosed herein supported blood flow rates sufficient to permit dialysis. Effective dialysis requires a blood flow that is marginally greater than the pump rate of the dialysis machine, or at least a blood rate adequate to prevent recirculation during dialysis. Also, the treated subjects individually displayed a reduced incidence of dehiscence defined as separation of the anastomotic vein or artery from the PTFE graft, and an improved integration of the prosthetic bridge defined as proliferation and/or migration of smooth muscle cells or endothelial cells into or within the lumen of the prosthetic bridge. Blood flow out of the A/V graft at the venous outflow site was comparable to that into the graft site. As used herein, comparable means substantially similar for clinical purposes. For example, the desired blood flow rate is about 150-500 mL/min, preferably about 300-500 mL/min, and more preferably about 350-400 mL/min.

Additionally, smooth muscle cell and/or endothelial cell migration into or within the prosthetic bridge will be measured as an indicia of integration. It is contemplated that the implantable material of the present invention will promote smooth muscle cell proliferation and endothelial cell proliferation, as well as migration of both into the bridge. Three five-micrometer sections through the PTFE graft may be obtained and stained for SMC actin and will be evaluated to identify SMC and Factor VIII (von Willebrands Factor) and/or PECAM-1 to identify endothelial cells. The endothelial cells will be quantitated using microscopy/morphometry and custom software.

Yet another indicia of a functioning A/V graft is adequate lumen diameter. The implants of the present invention permitted maintenance of adequate lumen diameter by reducing vessel stenosis and thereby permitting unimpeded blood flow at rates suitable for effective dialysis, i.e., effective dialysis requires a blood flow that is marginally greater than the pump rate of the dialysis machine, or at least a blood flow rate adequate to prevent recirculation during dialysis. Lumen diameter and percent stenosis were monitored using angiography of the arteriovenous graft anastomoses at the day of arteriovenous graft creation and just prior to 30-day sacrifice. Narrowing of the lumen post-surgery was correlated with blood flow rates using standard Doppler ultrasound protocols.

The implantable material of the present invention reduced the presence and degree of stenosis of the treated anastomoses compared to the control implants. Percent stenosis, determined by angiography, for each test subject treated in the study is presented below in Table 1. On average, the implantable material reduced stenosis by ninety-five percent, from 46% in control animals to 2.5% for those receiving implants comprising cells ([46−2.5]/46×100). The results will be confirmed histologically. These studies illustrate that the present invention prevented or delayed narrowing that reduces blood flow below a rate suitable for dialysis, thereby promoting the functionality of an A/V graft anastomosis.

TABLE 1

Summary of AV Graft Study

| Animal # | Group | Percent Stenosis (0° angle to graft) | Percent Stenosis (90° angle to graft) | Average Percent Stenosis |
|---|---|---|---|---|
| 1656 | 2 | 30% | 20% | 25% |
| 1657 | 2 | 80% | 80% | 80% |
| 1664 | 2 | 60% | 80% | 70% |
| 1667 | 2 | 0% | 20% | 10% |
| 1624 | 3 | ND | 0% | 0% |
| 1659 | 3 | 0% | 0% | 0% |
| 1666 | 3 | 0% | 20% | 10% |
| 1670 | 3 | 0% | 0% | 0% |

Group 2: Received control implant of biocompatible matrix alone.
Group 3: Received implantable material in a flexible planar form comprising cells and biocompatible matrix.

Example 3

Human AV Graft Clinical Study

This example provides experimental protocols for testing and using the invention to promote formation of a functional AV graft in human clinical test subjects. Using standard surgical procedures, an AV graft anastomosis is created at the desired anatomic location and an ePTFE prosthetic bridge is placed between the arterial and venous anastomoses. Implantable material is then disposed in the perivascular space adjacent to each surgically created AV graft anastomosis; the details of one exemplary procedure are set forth below. As described earlier, the placement and configuration of implantable material can be varied by the skilled practitioner in a routine manner.

Specifically, the study includes human test subjects undergoing AV graft surgery. Conventional AV graft surgery procedures will be performed according to standard operative techniques. The implantable material of the present invention will be applied to the AV graft anastomoses and surrounds as described below after the graft surgery is completed and flow through the graft is established.

Human clinical subjects will receive one or more portions of the implantable material on the day of surgery. Two to three such portions will be applied to each test subject. One portion of implantable material is wrapped around each anastomotic site. One end is then passed under the anastomotic segment until the middle of the wrap is at the point where the vessel and graft meet. Both ends are then wrapped around the suture line keeping the implant centered over the suture line. The ends can overlap to secure the material in place. An additional single portion of implantable material will be placed on the proximal venous segment of the arteriovenous graft, longitudinally along the length of the vein starting at the anastomosis, of each test subject. The implantable material does not need to completely wrap around the circumference of the vein.

The anastomotic sites will be treated with preferred implants, for example, as illustrated in FIGS. 4A, 4B and 4C, or as illustrated in FIG. 5. Additionally, in certain patients, the proximal venous segment (distal to the venous-arterial anastomosis) is treated by placing a preferred implant longitudinally along the length of vein starting at the anastomotic site. It is expected that the total cell load based on body weight will be approximately $2.0 \times 10^4$ cells per kg to approximately $6.0 \times 10^4$ cells per kg.

Clinical follow-ups will be performed at 5 days, 2 weeks and at 1, 3 and 6 months. Access flow measurements using color-flow Doppler ultrasound will be required at day 5 to establish a baseline level, followed at 2 weeks, 1 month, 3 months and 6 months post-surgery. Test subjects that exhibit an absolute flow of less than 350 mL/min, or greater than 25% reduction in flow from the previous measurement, or greater than 50% area stenosis (as measured by Doppler ultrasound) will be referred for angiography. Remedial clinical intervention such as angioplasty will be permitted for stenotic lesions of greater than 50% determined by angiography.

Contrast angiography of the graft, as well as the arterial and venous anastomotic sites, will be performed at baseline and at 3 months. Lumen diameter will be calculated for each region and peak systolic velocity will be measured.

Expected Results for Human AV Graft Clinical Study. It is expected that subjects treated with the implantable material of the present invention as described above will display one or more indicia of formation of a clinically functional AV graft. Specifically, the treated subjects individually will display, for example, an improved blood flow, up to at least a flow sufficient for dialysis (e.g. a blood flow within the range of 35-500 mL/min and preferably at least 350 ml/min.), a reduced incidence of dehiscence defined as separation of the anastomotic vein or artery from the PTFE graft, a reduced incidence of serous perigraft collections and pseudoaneurysm, and/or an improved integration of the prosthetic bridge defined as proliferation and/or migration of smooth muscle cells or endothelial cells into or within the lumen of the prosthetic bridge. Blood flow out of the AV graft at the venous outflow site will be comparable to that into the graft site. Comparable means substantially similar for clinical purposes. For example, the desired blood flow rate is about 150-500 mL/min, preferably about 300-500 mL/min, and more preferably about 350-400 mL/min.

Additionally, smooth muscle cell and/or endothelial cell migration into or within the prosthetic bridge will be measured by intravascular ultrasound as an indicia of integration. It is expected that the implantable material of the present invention when used as described herein will promote smooth muscle proliferation and/or endothelial cell proliferation, as well as migration of both into the bridge.

Yet another indicia of a functioning AV graft is adequate lumen diameter. It is expected that the implants of the present invention will permit maintenance of adequate lumen diameter thereby permitting unimpeded blood flow at rates suitable for effective dialysis, i.e., effective dialysis requires a blood flow that is marginally greater that the pump rate of the dialysis machine, or at least a blood rate adequate to prevent recirculation during dialysis. Lumen diameter will be monitored using angiography of the arteriovenous graft anastomosis at baseline (approximately 5 days post-arteriovenous graft creation) and thereafter at least 3 months post surgery. Narrowing of the lumen post-surgery will be correlated with blood flow rates using standard Doppler ultrasound protocols. It is expected that the present invention when used as described herein will prevent or delay narrowing that impedes blood flow below a rate suitable for dialysis as described herein.

In the case of AV grafts, it is expected that the implantable material of the present invention will prevent or reduce the incidence of dehiscence.

As a group, the treated subjects are expected to show at least incremental differences in at least one of these aforementioned indicia of functionality as compared to controls

Example 4

Peripheral Graft Study

This example provides experimental protocols for testing and using a preferred embodiment of the present invention to promote formation of a functional peripheral graft in test subjects. Using standard surgical procedures, a peripheral graft anastomosis is created at the desired anatomic location and an ePTFE prosthetic bridge is placed between the anastomoses. Implantable material is then disposed in the perivascular space adjacent to each surgically created peripheral graft anastomosis; the details of one exemplary procedure are set forth below. As described earlier, the placement and configuration of implantable material can be varied.

Specifically, the study includes test subjects undergoing peripheral graft surgery. Conventional peripheral graft surgery procedures will be performed according to standard operative techniques. Implantable material will be applied to the peripheral graft anastomoses and surrounds as described below after the graft surgery is completed and flow through the graft is established.

Test subjects will receive one or more preferred implantable materials on the day of surgery. Two to three such implants will be applied to each test subject. One such implant is wrapped around each anastomotic site. One end of the implantable material is then passed under the anastomotic segment until the middle of the wrap is at the point where the vessel and graft meet. The ends are then wrapped around the suture line keeping the implant centered over the suture line. The ends can overlap each other to secure the material in place. An additional single implant will be placed on the proximal venous segment of the peripheral graft, longitudinally along the length of the vein starting at the anastomosis, of each test subject. The implant does not need to completely wrap around the circumference of the vein.

The anastomotic sites will be wrapped with implantable material, for example, as illustrated in FIGS. 4A, 4B and 4C, or as illustrated in FIG. 5. Additionally, the proximal vessel segment (distal to the anastomosis) is treated by placing the implantable material longitudinally along the length of vessel starting at the anastomotic site. The total cell load based on body weight will be approximately $2.0 \times 10^4$ cells per kg to approximately $6.0 \times 10^4$ cells per kg.

Clinical follow-ups will be performed at 5 days, 2 weeks and at 1, 3 and 6 months. Blood flow measurements using color-flow Doppler ultrasound will be required at day 5 to establish a baseline level, followed at 2 weeks, 1 month, 3 months and 6 months post-surgery. Test subjects that exhibit an absolute flow of less than 350 mL/min, or greater than 25% reduction in flow from the previous measurement, or greater than 50% area stenosis (as measured by Doppler ultrasound) will be referred for angiography. Remedial clinical intervention such as angioplasty will be permitted for stenotic lesions of greater than 50% determined by angiography.

Contrast angiography of the graft, as well as the anastomotic sites, will be performed. Lumen diameter will be calculated for each region and peak systolic velocity will be measured.

Expected Results for Peripheral Graft Subjects. It is expected that subjects treated with the implantable material of the present invention as described above will display one or more indicia of formation of a clinically functional peripheral graft. Peripheral grafts treated in accordance with the materials and methods disclosed herein will support blood flow sufficient to restore or maintain clinically-acceptable blood circulation. Also, the treated subjects individually will display, for example, a reduced incidence of dehiscence defined as separation of the anastomotic vein from the PTFE graft, and/or an improved integration of the prosthetic bridge defined as proliferation and/or migration of smooth muscle cells or endothelial cells into or within the lumen of the prosthetic bridge. Blood flow out of the peripheral graft at the outflow site will be comparable to that into the graft site. As used herein, comparable means substantially similar for clinical purposes. For example, the desired blood flow rate is about 150-500 mL/min, preferably about 300-500 mL/min, and more preferably about 350-400 mL/min.

Additionally, smooth muscle cell and/or endothelial cell migration into or within the prosthetic bridge will be measured as an indicia of integration. It is expected that the implantable material of the present invention will promote smooth muscle proliferation and/or endothelial cell proliferation, as well as migration of both into the bridge.

Yet another indicia of a functioning peripheral graft is adequate lumen diameter. It is expected that the implants of the present invention will permit maintenance of adequate lumen diameter thereby permitting unimpeded blood flow at rates sufficient to maintain peripheral circulation. Lumen diameter will be monitored using angiography of the peripheral graft at baseline and at least 3 months post-graft creation. Narrowing of the lumen post-surgery will be correlated with blood flow rates using standard Doppler ultrasound protocols. It is expected that the implantable material of the present invention will prevent or delay narrowing that impedes blood flow below a rate suitable for peripheral circulation as described herein.

In the case of peripheral bypass grafts, it is expected that treatment with the implantable material of the present invention will result in blood flow rates permitting clinically-acceptable circulation, or approximating normal rates. Flow into and out of the graft will be comparable. Comparable means substantially similar for clinical purposes. For example, the desired blood flow rate is about 150-500 mL/min, preferably about 300-500 mL/min, and more preferably about 350-400 mL/min. Additionally, it is expected that treatment will promote proliferation and migration of smooth muscle cells and/or endothelial cells into the prosthetic or native graft.

In the case of peripheral bypass grafts, it is expected that the implantable material of the present invention will prevent or reduce the incidence of dehiscence.

As a group, the treated subjects are expected to show at least incremental differences in at least one of these aforementioned indicia of functionality as compared to controls The invention may be embodied in other specific forms without departing from the spirit or essential characteristics thereof. The present embodiments are therefore to be considered illustrative and not restrictive, the scope of the invention being indicated by the appended claims rather than by the foregoing description, and all changes which come within the meaning and range of equivalency of the claims are therefore intended to be embraced therein.

What is claimed is:

1. An implantable material prepared by a method comprising the steps of:
    cryopreserving at $-4°$ C. to $-160°$ C. for at least 1 month a population of vascular endothelial cells having an inhibitory phenotype such that they are capable of inhibiting or interfering with vascular smooth muscle cell proliferation, said cells attached via cell to matrix interactions to a flexible planar or flowable biocompatible substrate, wherein said inhibitory phenotype is selected from the group consisting of: expression of heparin sulfate of at least 200 ng/mL/day, expression of TGF-beta of at least 300 pg/mL/day, and expression of b-FGF of no more than 300 pg/mL/day; and wherein said population of cells is at least 80% viable prior to and following cryopreservation; and thawing said cryopreserved implantable material in a transport media composition comprising EGM-2 supplemented with an amount of VEGF sufficient to maintain both cell viability and said inhibitory phenotype for an extended period of time when said implantable material is stored at temperatures below the cells' standard cell culture temperature.

2. The implantable material of claim 1 wherein said material has been cryopreserved at −4° C. to −160° C. for at least 6 months.

3. The implantable material of claim 1 wherein said material has been cryopreserved at −4° C. to −160° C. for at least 12 months.

4. The implantable material of claim 1 wherein said material is in a non-frozen state for up to 7 days.

5. The implantable material of claim 1 wherein said material is in a non-frozen state for at least 14 days.

6. The implantable material of claim 1 wherein said material is in a non-frozen state for at least 21 days.

7. The implantable material of claim 1 wherein said material is in a non-frozen state for at least 28 days.

8. The implantable material of claim 1 wherein said material is stored at or below 37° C.

9. The implantable material of claim 1 wherein said material is stored at 15-25° C.

10. The implantable material of claim 1 wherein said population of cells is not immortalized.

11. The implantable material of claim 1 wherein the amount of VEGF is 2 ng/mL to 4 ng/mL and the extended period is one week.

12. A composition for treatment comprising the implantable material of claim 1, characterized in that said composition is implanted in a patient in need thereof in a non-frozen state.

13. The composition of claim 12 wherein said composition is implanted 1 week to 1 year after a non-frozen state is achieved.

14. A cryopreserved implantable material comprising:
a biocompatible matrix engrafted with a population of near-confluent, confluent, or post-confluent vascular endothelial cells, wherein the implantable material is cryopreserved at −4° C. to −160° C. for at least 1 month, and wherein the cells are at least 80% viable and exhibit a phenotype comprising heparan sulfate production of at least 200 ng/mL/day, TGF-$\beta$1 production of at least 300 pg/mL/day, and b-FGF production of no more than 300 pg/mL/day, prior to and following cryopreservation; and, a transport media composition comprising EGM-2 supplemented with an amount of VEGF sufficient to maintain both cell viability and said inhibitory phenotype for an extended period of time when said implantable material is stored at temperatures below the cells' standard cell culture temperature.

15. The cryopreserved implantable material of claim 14 wherein the material is cryopreserved at −4° C. to −160° C. for at least 6 months.

16. The cryopreserved implantable material of claim 14 wherein the material is cryopreserved at −4° C. to −160° C. for at least 12 months.

17. The cryopreserved implantable material of claim 14 wherein the amount of VEGF is 2 ng/mL to 4 ng/mL and the extended period is one week.

* * * * *